(12) United States Patent
Tang et al.

(10) Patent No.: US 11,053,317 B2
(45) Date of Patent: Jul. 6, 2021

(54) PHARMACEUTICAL PREPARATION STABLY COMPRISING CD147 MONOCLONAL ANTIBODY

(71) Applicant: JIANGSU PACIFIC MEINUOKE BIO-PHARMACEUTICAL CO., LTD., Jiangsu (CN)

(72) Inventors: Hao Tang, Changzhou (CN); Qiang Feng, Changzhou (CN); Xiaochun Chen, Changzhou (CN)

(73) Assignee: JIANGSU PACIFIC MEINUOKE BIO-PHARMACEUTICAL CO., LTD., Jiangsu (CN)

( * ) Notice: Subject to any disclaimer, the term of this patent is extended or adjusted under 35 U.S.C. 154(b) by 0 days.

(21) Appl. No.: 16/461,800

(22) PCT Filed: Dec. 27, 2017

(86) PCT No.: PCT/CN2017/118893
§ 371 (c)(1),
(2) Date: May 17, 2019

(87) PCT Pub. No.: WO2018/121578
PCT Pub. Date: Jul. 5, 2018

(65) Prior Publication Data
US 2019/0359709 A1    Nov. 28, 2019

(30) Foreign Application Priority Data
Dec. 30, 2016 (CN) .......................... 201611271126.8

(51) Int. Cl.
| C07K 16/28 | (2006.01) |
| A61K 9/08 | (2006.01) |
| A61K 47/12 | (2006.01) |
| A61K 47/22 | (2006.01) |
| A61K 47/26 | (2006.01) |
| A61K 9/00 | (2006.01) |

(52) U.S. Cl.
CPC ........ *C07K 16/2803* (2013.01); *A61K 9/0019* (2013.01); *A61K 9/08* (2013.01); *A61K 47/12* (2013.01); *A61K 47/22* (2013.01); *A61K 47/26* (2013.01); *C07K 2317/94* (2013.01)

(58) Field of Classification Search
None
See application file for complete search history.

(56) References Cited

U.S. PATENT DOCUMENTS

| 8,618,264 B2 * | 12/2013 | Cunningham ..... C07K 16/2803 530/387.3 |
| 9,963,506 B2 * | 5/2018 | Chen .................. C07K 16/2803 |
| 2006/0104974 A1 * | 5/2006 | Davis ...................... A61P 35/02 424/144.1 |
| 2008/0071063 A1 * | 3/2008 | Allan .................. C07K 16/2866 530/387.1 |
| 2009/0162352 A1 * | 6/2009 | Adler .................. A61K 39/3955 424/133.1 |
| 2011/0223176 A1 * | 9/2011 | Barlow .............. C07K 16/2803 424/143.1 |
| 2016/0271253 A1 | 9/2016 | Chang |

FOREIGN PATENT DOCUMENTS

| CN | 1381461 A | 11/2002 |
| CN | 101426527 A | 5/2009 |
| CN | 101598731 A | 12/2009 |
| CN | 101896163 A | 11/2010 |
| CN | 102918056 A | 2/2013 |
| CN | 102961745 A | 3/2013 |
| CN | 104086654 A | 10/2014 |
| CN | 102961745 B | 2/2015 |
| CN | 105126099 A | 12/2015 |
| CN | 105431453 A | 3/2016 |
| WO | 2015/160853 A2 | 10/2015 |
| WO | 2018/121580 A1 | 7/2018 |

OTHER PUBLICATIONS

Zhang, D. W. et al., "HAb18G/CD147 promotes activation of hepatic stellate cells and is a target for antibody therapy of liver fibrosis", Journal of Hepatology (2012), vol. 57(6), pp. 1283-1291.
Chen, Y. et al., "Human Tumor Cells Induce Angiogenesis through Positive Feedback between CD147 and Insulin-Like Growth Factor-I", PLoS One (2012). vol. 7(7), e40965, pp. 1-11.
Tang, J. et al., "CD147 induces UPR to inhibit apoptosis and chemosensitivity by increasing the transcription of Bip in hepatocellular carcinoma", Cell Death and Differentiation (2012), vol. 19(11), pp. 1779-1790.
Li, Y. et al., "Extracellular Membrane-proximal Domain of HAb18G/CD147 Binds to Metal Ion-dependent Adhesion Site (MIDAS) Motif of Integrin β1 to Modulate Malignant Properties of Hepatoma Cells", The Journal of Biological Chemistry (2012), vol. 287(7), pp. 4759-4772.
Wu, J. et al., "HAb18G/CD147 promotes epithelial-mesenchymal transition through TGF-β signaling and is transcriptionally regulated by Slug", Oncogene (2011). vol. 30(43), pp. 1-18.

(Continued)

*Primary Examiner* — Marianne P Allen
(74) *Attorney, Agent, or Firm* — Jun He Law Offices P.C.; Zhaohui Wang

(57) ABSTRACT

Disclosed is a pharmaceutical preparation comprising a CD147 monoclonal antibody, a buffer, a protein protectant and a surfactant. The pharmaceutical preparation can maintain the stability of the CD147 monoclonal antibody over a long period of time. Also disclosed are the use of the pharmaceutical preparation in the preparation of a drug for treating CD147-related diseases, in particular non-small cell lung cancer, and a method for preparing the pharmaceutical preparation.

3 Claims, 2 Drawing Sheets
Specification includes a Sequence Listing.

(56) References Cited

OTHER PUBLICATIONS

Zhao, P. et al., "HAb18G/CD147 promotes cell motility by regulating annexin II-activated RhoA and Rac1 signaling pathways in hepatocellular carcinoma cells", Hepatology (2011), vol. 54(6), pp. 2012-2024.

Zhao, P. et al., "Annexin II promotes invasion and migration of human hepatocellular carcinoma cells in vitro via its interaction with HAb18G/CD147", Cancer Science (2010), vol. 101(2), pp. 387-395.

Gou, X. et al., "HAb18G/CD147 inhibits starvation-induced autophagy in human hepatoma cell SMMC7721 with an involvement of Beclin 1 down-regulation", Cancer Science (2009), vol. 100(5), pp. 837-843.

Chen, Y. et al., "Upregulation of HAb18G/CD147 in activated human umbilical vein endothelial cells enhances the angiogenesis", Cancer Letters (2009), vol. 278(1), pp. 113-121.

Wang W et al: "Antibody Structure, Instability, and Formulation", Journal of Pharmaceutical Sciences, American Chemical Society and American Pharmaceutical Association, US, vol. 96, No. 1, Jan. 1, 2007 (Jan. 1, 2007), pp. 1-26, XP009084505, ISSN: 0022-3549, DOI: 10.1002/JPS.20727. p. 14, right column.

Daugherty Ann L et al: "Chapter 8: Formulation and delivery issues for monoclonal antibody therapeutics", Jan. 1, 2010 (Jan. 1, 2010), Current Trends in Monoclonal Antibody Development and Manufacturing, Springer, US, pp. 103-129, XP009180430, DOI: 10.1007/978-0-387-76643-0_8. first paragraph of chapter 4, p. 107.

The partial supplementary European search report of European application No. 17887476.4, dated Nov. 27, 2020.

The First Office Action for Chinese Patent Application No. 201711441910.3, dated Apr. 20, 2021.

\* cited by examiner

```
                    SEQUENCE LISTING

<160> NUMBER OF SEQ ID NOS: 22

<210> SEQ ID NO 1
<211> LENGTH: 10
<212> TYPE: PRT
<213> ORGANISM: Artificial Sequence
<220> FEATURE:
<223> OTHER INFORMATION: CDR1 of heavy chain of monoclonal anti-CD147
      antibody

<400> SEQUENCE: 1

Gly Phe Thr Phe Ser Asp Ala Trp Met Asp
1               5                   10

<210> SEQ ID NO 2
<211> LENGTH: 19
<212> TYPE: PRT
<213> ORGANISM: Artificial Sequence
<220> FEATURE:
<223> OTHER INFORMATION: CDR2 of heavy chain of monoclonal anti-CD147
      antibody

<400> SEQUENCE: 2

Glu Ile Arg Ser Lys Ala Asn Asn His Ala Pro Tyr Tyr Thr Glu Ser
1               5                   10                  15

Val Lys Gly

<210> SEQ ID NO 3
```

```
<211> LENGTH: 7
<212> TYPE: PRT
<213> ORGANISM: Artificial Sequence
<220> FEATURE:
<223> OTHER INFORMATION: CDR3 of heavy chain of monoclonal anti-CD147
      antibody

<400> SEQUENCE: 3

Arg Asp Ser Thr Ala Thr His
1               5

<210> SEQ ID NO 4
<211> LENGTH: 11
<212> TYPE: PRT
<213> ORGANISM: Artificial Sequence
<220> FEATURE:
<223> OTHER INFORMATION: CDR1 of light chain of monoclonal anti-CD147
      antibody

<400> SEQUENCE: 4

Lys Ala Ser Gln Ser Val Ile Asn Asp Val Ala
1               5                   10

<210> SEQ ID NO 5
<211> LENGTH: 7
<212> TYPE: PRT
<213> ORGANISM: Artificial Sequence
<220> FEATURE:
<223> OTHER INFORMATION: CDR2 of light chain of monoclonal anti-CD147
      antibody

<400> SEQUENCE: 5

Tyr Ala Ser Asn Arg Asn Thr
1               5

<210> SEQ ID NO 6
<211> LENGTH: 9
<212> TYPE: PRT
<213> ORGANISM: Artificial Sequence
<220> FEATURE:
<223> OTHER INFORMATION: CDR3 of light chain of monoclonal anti-CD147
      antibody

<400> SEQUENCE: 6

Gln Gln Asp Tyr Ser Pro Pro Phe Thr
1               5

<210> SEQ ID NO 7
<211> LENGTH: 117
<212> TYPE: PRT
<213> ORGANISM: Artificial Sequence
<220> FEATURE:
<223> OTHER INFORMATION: heavy chain variable region VH of monoclonal
      anti-CD147 antibody

<400> SEQUENCE: 7

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Ala
                20                  25                  30

Trp Met Asp Trp Val Arg Gln Ser Pro Glu Lys Gly Leu Glu Trp Val
            35                  40                  45

Ala Glu Ile Arg Ser Lys Ala Asn Asn His Ala Pro Tyr Tyr Thr Glu
        50                  55                  60

Ser Val Lys Gly Arg Phe Thr Ile Ser Arg Asp Asp Ser Lys Ser Ile
65                  70                  75                  80
```

Ile Tyr Leu Gln Met Asn Asn Leu Arg Ala Glu Asp Thr Gly Ile Tyr
                85                  90                  95

Tyr Cys Thr Arg Asp Ser Thr Ala Thr His Trp Gly Gln Gly Thr Leu
            100                 105                 110

Val Thr Val Ser Ala
        115

<210> SEQ ID NO 8
<211> LENGTH: 133
<212> TYPE: PRT
<213> ORGANISM: Artificial Sequence
<220> FEATURE:
<223> OTHER INFORMATION: heavy chain variable region VH of monoclonal
      anti-CD147 antibody

<400> SEQUENCE: 8

Met Gly Trp Ser Cys Ile Ile Leu Phe Leu Val Ala Thr Ala Thr Gly
1               5                   10                  15

Glu Val Lys Leu Glu Glu Ser Gly Gly Gly Leu Val Gln Pro Gly Gly
            20                  25                  30

Ser Met Lys Leu Ser Cys Val Ala Ser Gly Phe Thr Phe Ser Asp Ala
        35                  40                  45

Trp Met Asp Trp Val Arg Gln Ser Pro Glu Lys Gly Leu Glu Trp Val
    50                  55                  60

Ala Glu Ile Arg Ser Lys Ala Asn Asn His Ala Pro Tyr Tyr Thr Glu
65                  70                  75                  80

Ser Val Lys Gly Arg Phe Thr Ile Ser Arg Asp Asp Ser Lys Ser Ile
                85                  90                  95

Ile Tyr Leu Gln Met Asn Asn Leu Arg Ala Glu Asp Thr Gly Ile Tyr
            100                 105                 110

Tyr Cys Thr Arg Asp Ser Thr Ala Thr His Trp Gly Gln Gly Thr Leu
        115                 120                 125

Val Thr Val Ser Ala
    130

<210> SEQ ID NO 9
<211> LENGTH: 111
<212> TYPE: PRT
<213> ORGANISM: Artificial Sequence
<220> FEATURE:
<223> OTHER INFORMATION: heavy chain variable region VH of monoclonal
      anti-CD147 antibody

<400> SEQUENCE: 9

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Pro Tyr Tyr Thr Glu
    50                  55                  60

Ser Val Lys Gly Arg Phe Thr Ile Ser Arg Asp Asp Ser Lys Ser Ile
65                  70                  75                  80

Ile Tyr Leu Gln Met Asn Asn Leu Arg Ala Glu Asp Thr Gly Ile Tyr
                85                  90                  95

Tyr Cys Thr Arg Asp Ser Thr Ala Thr His Trp Gly Gln Gly Thr
            100                 105                 110

<210> SEQ ID NO 10
<211> LENGTH: 127
<212> TYPE: PRT
<213> ORGANISM: Artificial Sequence
<220> FEATURE:
<223> OTHER INFORMATION: heavy chain variable region VH of monoclonal anti-CD147 antibody

<400> SEQUENCE: 10

```
Met Gly Trp Ser Cys Ile Ile Leu Phe Leu Val Ala Thr Ala Thr Gly
1               5                   10                  15

Glu Val Lys Leu Glu Glu Ser Gly Gly Gly Leu Val Gln Pro Gly Gly
            20                  25                  30

Ser Met Lys Leu Ser Cys Val Ala Ser Gly Phe Thr Phe Ser Asp Ala
        35                  40                  45

Trp Met Asp Trp Val Arg Gln Ser Pro Glu Lys Gly Leu Glu Trp Val
    50                  55                  60

Ala Glu Ile Arg Ser Lys Ala Asn Asn His Ala Pro Tyr Tyr Thr Glu
65                  70                  75                  80

Ser Val Lys Gly Arg Phe Thr Ile Ser Arg Asp Asp Ser Lys Ser Ile
                85                  90                  95

Ile Tyr Leu Gln Met Asn Asn Leu Arg Ala Glu Asp Thr Gly Ile Tyr
            100                 105                 110

Tyr Cys Thr Arg Asp Ser Thr Ala Thr His Trp Gly Gln Gly Thr
        115                 120                 125
```

<210> SEQ ID NO 11
<211> LENGTH: 108
<212> TYPE: PRT
<213> ORGANISM: Artificial Sequence
<220> FEATURE:
<223> OTHER INFORMATION: light chain variable region VL of monoclonal anti-CD147 antibody

<400> SEQUENCE: 11

```
Ser Ile Val Met Thr Gln Thr Pro Thr Phe Leu Val Val Ser Ala Gly
1               5                   10                  15

Asp Arg Val Thr Ile Thr Cys Lys Ala Ser Gln Ser Val Ile Asn Asp
            20                  25                  30

Val Ala Trp Tyr Gln Gln Lys Pro Gly Gln Ser Pro Lys Leu Leu Ile
        35                  40                  45

Phe Tyr Ala Ser Asn Arg Asn Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Pro Pro Phe
                85                  90                  95

Thr Phe Gly Ser Gly Thr Lys Leu Glu Ile Lys Arg
            100                 105
```

<210> SEQ ID NO 12
<211> LENGTH: 124
<212> TYPE: PRT
<213> ORGANISM: Artificial Sequence
<220> FEATURE:
<223> OTHER INFORMATION: light chain variable region VL of monoclonal anti-CD147 antibody

<400> SEQUENCE: 12

```
Met Gly Trp Ser Cys Ile Ile Leu Phe Leu Val Ala Thr Ala Thr Gly
1               5                   10                  15

Ser Ile Val Met Thr Gln Thr Pro Thr Phe Leu Val Val Ser Ala Gly
            20                  25                  30

Asp Arg Val Thr Ile Thr Cys Lys Ala Ser Gln Ser Val Ile Asn Asp
        35                  40                  45

Val Ala Trp Tyr Gln Gln Lys Pro Gly Gln Ser Pro Lys Leu Leu Ile
    50                  55                  60

Phe Tyr Ala Ser Asn Arg Asn Thr Gly Val Pro Asp Arg Phe Thr Gly
65                  70                  75                  80

Ser Gly Tyr Gly Thr Asp Phe Thr Phe Thr Ile Ser Thr Val Gln Ala
                85                  90                  95

Glu Asp Leu Ala Val Tyr Phe Cys Gln Gln Asp Tyr Ser Pro Pro Phe
            100                 105                 110

Thr Phe Gly Ser Gly Thr Lys Leu Glu Ile Lys Arg
            115                 120
```

<210> SEQ ID NO 13
<211> LENGTH: 103
<212> TYPE: PRT
<213> ORGANISM: Artificial Sequence
<220> FEATURE:
<223> OTHER INFORMATION: light chain variable region VL of monoclonal anti-CD147 antibody

<400> SEQUENCE: 13

```
Ser Ile Val Met Thr Gln Thr Pro Thr Phe Leu Val Val Ser Ala Gly
1               5                   10                  15

Asp Arg Val Thr Ile Thr Cys Lys Ala Ser Gln Ser Val Ile Asn Asp
            20                  25                  30

Val Ala Trp Tyr Gln Gln Lys Pro Gly Gln Ser Pro Lys Leu Leu Ile
        35                  40                  45

Phe Tyr Ala Ser Asn Arg Asn Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Pro Pro Phe
                85                  90                  95

Thr Phe Gly Ser Gly Thr Lys
            100
```

<210> SEQ ID NO 14
<211> LENGTH: 119
<212> TYPE: PRT
<213> ORGANISM: Artificial Sequence
<220> FEATURE:
<223> OTHER INFORMATION: light chain variable region VL of monoclonal anti-CD147 antibody

<400> SEQUENCE: 14

```
Met Gly Trp Ser Cys Ile Ile Leu Phe Leu Val Ala Thr Ala Thr Gly
1               5                   10                  15

Ser Ile Val Met Thr Gln Thr Pro Thr Phe Leu Val Val Ser Ala Gly
            20                  25                  30

Asp Arg Val Thr Ile Thr Cys Lys Ala Ser Gln Ser Val Ile Asn Asp
        35                  40                  45

Val Ala Trp Tyr Gln Gln Lys Pro Gly Gln Ser Pro Lys Leu Leu Ile
    50                  55                  60
```

```
Phe Tyr Ala Ser Asn Arg Asn Thr Gly Val Pro Asp Arg Phe Thr Gly
 65                  70                  75                  80

Ser Gly Tyr Gly Thr Asp Phe Thr Phe Thr Ile Ser Thr Val Gln Ala
                 85                  90                  95

Glu Asp Leu Ala Val Tyr Phe Cys Gln Gln Asp Tyr Ser Pro Pro Phe
            100                 105                 110

Thr Phe Gly Ser Gly Thr Lys
            115

<210> SEQ ID NO 15
<211> LENGTH: 447
<212> TYPE: PRT
<213> ORGANISM: Artificial Sequence
<220> FEATURE:
<223> OTHER INFORMATION: heavy chain of monoclonal anti-CD147 antibody

<400> SEQUENCE: 15

Glu Val Lys Leu Glu Glu Ser Gly Gly Gly Leu Val Gln Pro Gly Gly
  1               5                  10                  15

Ser Met Lys Leu Ser Cys Val Ala Ser Gly Phe Thr Phe Ser Asp Ala
             20                  25                  30

Trp Met Asp Trp Val Arg Gln Ser Pro Glu Lys Gly Leu Glu Trp Val
         35                  40                  45

Ala Glu Ile Arg Ser Lys Ala Asn Asn His Ala Pro Tyr Tyr Thr Glu
 50                  55                  60

Ser Val Lys Gly Arg Phe Thr Ile Ser Arg Asp Asp Ser Lys Ser Ile
 65                  70                  75                  80

Ile Tyr Leu Gln Met Asn Asn Leu Arg Ala Glu Asp Thr Gly Ile Tyr
             85                  90                  95

Tyr Cys Thr Arg Asp Ser Thr Ala Thr His Trp Gly Gln Gly Thr Leu
            100                 105                 110

Val Thr Val Ser Ala Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
            165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300
```

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Arg Asp Glu Leu Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 16
<211> LENGTH: 463
<212> TYPE: PRT
<213> ORGANISM: Artificial Sequence
<220> FEATURE:
<223> OTHER INFORMATION: heavy chain of monoclonal anti-CD147 antibody

<400> SEQUENCE: 16

Met Gly Trp Ser Cys Ile Ile Leu Phe Leu Val Ala Thr Ala Thr Gly
1               5                   10                  15

Glu Val Lys Leu Glu Glu Ser Gly Gly Gly Leu Val Gln Pro Gly Gly
            20                  25                  30

Ser Met Lys Leu Ser Cys Val Ala Ser Gly Phe Thr Phe Ser Asp Ala
            35                  40                  45

Trp Met Asp Trp Val Arg Gln Ser Pro Glu Lys Gly Leu Glu Trp Val
    50                  55                  60

Ala Glu Ile Arg Ser Lys Ala Asn Asn His Ala Pro Tyr Tyr Thr Glu
65                  70                  75                  80

Ser Val Lys Gly Arg Phe Thr Ile Ser Arg Asp Asp Ser Lys Ser Ile
                85                  90                  95

Ile Tyr Leu Gln Met Asn Asn Leu Arg Ala Glu Asp Thr Gly Ile Tyr
            100                 105                 110

Tyr Cys Thr Arg Asp Ser Thr Ala Thr His Trp Gly Gln Gly Thr Leu
            115                 120                 125

Val Thr Val Ser Ala Ala Ser Thr Lys Gly Pro Ser Val Phe Pro Leu
    130                 135                 140

Ala Pro Ser Ser Lys Ser Thr Ser Gly Gly Thr Ala Ala Leu Gly Cys
145                 150                 155                 160

Leu Val Lys Asp Tyr Phe Pro Glu Pro Val Thr Val Ser Trp Asn Ser
                165                 170                 175

Gly Ala Leu Thr Ser Gly Val His Thr Phe Pro Ala Val Leu Gln Ser
            180                 185                 190

Ser Gly Leu Tyr Ser Leu Ser Ser Val Val Thr Val Pro Ser Ser Ser
            195                 200                 205

Leu Gly Thr Gln Thr Tyr Ile Cys Asn Val Asn His Lys Pro Ser Asn
    210                 215                 220

-continued

```
Thr Lys Val Asp Lys Arg Val Glu Pro Lys Ser Cys Asp Lys Thr His
225                 230                 235                 240

Thr Cys Pro Pro Cys Pro Ala Pro Glu Leu Leu Gly Gly Pro Ser Val
            245                 250                 255

Phe Leu Phe Pro Pro Lys Pro Lys Asp Thr Leu Met Ile Ser Arg Thr
        260                 265                 270

Pro Glu Val Thr Cys Val Val Val Asp Val Ser His Glu Asp Pro Glu
    275                 280                 285

Val Lys Phe Asn Trp Tyr Val Asp Gly Val Glu Val His Asn Ala Lys
290                 295                 300

Thr Lys Pro Arg Glu Glu Gln Tyr Asn Ser Thr Tyr Arg Val Val Ser
305                 310                 315                 320

Val Leu Thr Val Leu His Gln Asp Trp Leu Asn Gly Lys Glu Tyr Lys
            325                 330                 335

Cys Lys Val Ser Asn Lys Ala Leu Pro Ala Pro Ile Glu Lys Thr Ile
        340                 345                 350

Ser Lys Ala Lys Gly Gln Pro Arg Glu Pro Gln Val Tyr Thr Leu Pro
    355                 360                 365

Pro Ser Arg Asp Glu Leu Thr Lys Asn Gln Val Ser Leu Thr Cys Leu
370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
            405                 410                 415

Asp Gly Ser Phe Phe Leu Tyr Ser Lys Leu Thr Val Asp Lys Ser Arg
        420                 425                 430

Trp Gln Gln Gly Asn Val Phe Ser Cys Ser Val Met His Glu Ala Leu
    435                 440                 445

His Asn His Tyr Thr Gln Lys Ser Leu Ser Leu Ser Pro Gly Lys
450                 455                 460

<210> SEQ ID NO 17
<211> LENGTH: 441
<212> TYPE: PRT
<213> ORGANISM: Artificial Sequence
<220> FEATURE:
<223> OTHER INFORMATION: heavy chain of monoclonal anti-CD147 antibody

<400> SEQUENCE: 17

Glu Val Lys Leu Glu Glu Ser Gly Gly Gly Leu Val Gln Pro Gly Gly
1               5                   10                  15

Ser Met Lys Leu Ser Cys Val Ala Ser Gly Phe Thr Phe Ser Asp Ala
            20                  25                  30

Trp Met Asp Trp Val Arg Gln Ser Pro Glu Lys Gly Leu Glu Trp Val
        35                  40                  45

Ala Glu Ile Arg Ser Lys Ala Asn Asn His Ala Pro Tyr Tyr Thr Glu
    50                  55                  60

Ser Val Lys Gly Arg Phe Thr Ile Ser Arg Asp Asp Ser Lys Ser Ile
65                  70                  75                  80

Ile Tyr Leu Gln Met Asn Asn Leu Arg Ala Glu Asp Thr Gly Ile Tyr
            85                  90                  95

Tyr Cys Thr Arg Asp Ser Thr Ala Thr His Trp Gly Gln Gly Thr Ala
        100                 105                 110

Ser Thr Lys Gly Pro Ser Val Phe Pro Leu Ala Pro Ser Ser Lys Ser
    115                 120                 125
```

Thr Ser Gly Gly Thr Ala Ala Leu Gly Cys Leu Val Lys Asp Tyr Phe
130                 135                 140

Pro Glu Pro Val Thr Val Ser Trp Asn Ser Gly Ala Leu Thr Ser Gly
145                 150                 155                 160

Val His Thr Phe Pro Ala Val Leu Gln Ser Ser Gly Leu Tyr Ser Leu
                165                 170                 175

Ser Ser Val Val Thr Val Pro Ser Ser Ser Leu Gly Thr Gln Thr Tyr
            180                 185                 190

Ile Cys Asn Val Asn His Lys Pro Ser Asn Thr Lys Val Asp Lys Arg
        195                 200                 205

Val Glu Pro Lys Ser Cys Asp Lys Thr His Thr Cys Pro Pro Cys Pro
210                 215                 220

Ala Pro Glu Leu Leu Gly Gly Pro Ser Val Phe Leu Phe Pro Pro Lys
225                 230                 235                 240

Pro Lys Asp Thr Leu Met Ile Ser Arg Thr Pro Glu Val Thr Cys Val
                245                 250                 255

Val Val Asp Val Ser His Glu Asp Pro Glu Val Lys Phe Asn Trp Tyr
            260                 265                 270

Val Asp Gly Val Glu Val His Asn Ala Lys Thr Lys Pro Arg Glu Glu
        275                 280                 285

Gln Tyr Asn Ser Thr Tyr Arg Val Val Ser Val Leu Thr Val Leu His
290                 295                 300

Gln Asp Trp Leu Asn Gly Lys Glu Tyr Lys Cys Lys Val Ser Asn Lys
305                 310                 315                 320

Ala Leu Pro Ala Pro Ile Glu Lys Thr Ile Ser Lys Ala Lys Gly Gln
                325                 330                 335

Pro Arg Glu Pro Gln Val Tyr Thr Leu Pro Pro Ser Arg Asp Glu Leu
            340                 345                 350

Thr Lys Asn Gln Val Ser Leu Thr Cys Leu Val Lys Gly Phe Tyr Pro
        355                 360                 365

Ser Asp Ile Ala Val Glu Trp Glu Ser Asn Gly Gln Pro Glu Asn Asn
370                 375                 380

Tyr Lys Thr Thr Pro Pro Val Leu Asp Ser Asp Gly Ser Phe Phe Leu
385                 390                 395                 400

Tyr Ser Lys Leu Thr Val Asp Lys Ser Arg Trp Gln Gln Gly Asn Val
                405                 410                 415

Phe Ser Cys Ser Val Met His Glu Ala Leu His Asn His Tyr Thr Gln
            420                 425                 430

Lys Ser Leu Ser Leu Ser Pro Gly Lys
        435                 440

<210> SEQ ID NO 18
<211> LENGTH: 457
<212> TYPE: PRT
<213> ORGANISM: Artificial Sequence
<220> FEATURE:
<223> OTHER INFORMATION: heavy chain of monoclonal anti-CD147 antibody

<400> SEQUENCE: 18

Met Gly Trp Ser Cys Ile Ile Leu Phe Leu Val Ala Thr Ala Thr Gly
1               5                   10                  15

Glu Val Lys Leu Glu Glu Ser Gly Gly Gly Leu Val Gln Pro Gly Gly
            20                  25                  30

Ser Met Lys Leu Ser Cys Val Ala Ser Gly Phe Thr Phe Ser Asp Ala
        35                  40                  45

```
Trp Met Asp Trp Val Arg Gln Ser Pro Glu Lys Gly Leu Glu Trp Val
    50                  55                  60
Ala Glu Ile Arg Ser Lys Ala Asn Asn His Ala Pro Tyr Tyr Thr Glu
65                  70                  75                  80
Ser Val Lys Gly Arg Phe Thr Ile Ser Arg Asp Asp Ser Lys Ser Ile
                85                  90                  95
Ile Tyr Leu Gln Met Asn Asn Leu Arg Ala Glu Asp Thr Gly Ile Tyr
                100                 105                 110
Tyr Cys Thr Arg Asp Ser Thr Ala Thr His Trp Gly Gln Gly Thr Ala
                115                 120                 125
Ser Thr Lys Gly Pro Ser Val Phe Pro Leu Ala Pro Ser Ser Lys Ser
    130                 135                 140
Thr Ser Gly Gly Thr Ala Ala Leu Gly Cys Leu Val Lys Asp Tyr Phe
145                 150                 155                 160
Pro Glu Pro Val Thr Val Ser Trp Asn Ser Gly Ala Leu Thr Ser Gly
                165                 170                 175
Val His Thr Phe Pro Ala Val Leu Gln Ser Ser Gly Leu Tyr Ser Leu
                180                 185                 190
Ser Ser Val Val Thr Val Pro Ser Ser Ser Leu Gly Thr Gln Thr Tyr
                195                 200                 205
Ile Cys Asn Val Asn His Lys Pro Ser Asn Thr Lys Val Asp Lys Arg
    210                 215                 220
Val Glu Pro Lys Ser Cys Asp Lys Thr His Thr Cys Pro Pro Cys Pro
225                 230                 235                 240
Ala Pro Glu Leu Leu Gly Gly Pro Ser Val Phe Leu Phe Pro Pro Lys
                245                 250                 255
Pro Lys Asp Thr Leu Met Ile Ser Arg Thr Pro Glu Val Thr Cys Val
                260                 265                 270
Val Val Asp Val Ser His Glu Asp Pro Glu Val Lys Phe Asn Trp Tyr
            275                 280                 285
Val Asp Gly Val Glu Val His Asn Ala Lys Thr Lys Pro Arg Glu Glu
    290                 295                 300
Gln Tyr Asn Ser Thr Tyr Arg Val Val Ser Val Leu Thr Val Leu His
305                 310                 315                 320
Gln Asp Trp Leu Asn Gly Lys Glu Tyr Lys Cys Lys Val Ser Asn Lys
                325                 330                 335
Ala Leu Pro Ala Pro Ile Glu Lys Thr Ile Ser Lys Ala Lys Gly Gln
                340                 345                 350
Pro Arg Glu Pro Gln Val Tyr Thr Leu Pro Pro Ser Arg Asp Glu Leu
            355                 360                 365
Thr Lys Asn Gln Val Ser Leu Thr Cys Leu Val Lys Gly Phe Tyr Pro
    370                 375                 380
Ser Asp Ile Ala Val Glu Trp Glu Ser Asn Gly Gln Pro Glu Asn Asn
385                 390                 395                 400
Tyr Lys Thr Thr Pro Pro Val Leu Asp Ser Asp Gly Ser Phe Phe Leu
                405                 410                 415
Tyr Ser Lys Leu Thr Val Asp Lys Ser Arg Trp Gln Gln Gly Asn Val
            420                 425                 430
Phe Ser Cys Ser Val Met His Glu Ala Leu His Asn His Tyr Thr Gln
    435                 440                 445
Lys Ser Leu Ser Leu Ser Pro Gly Lys
    450                 455
```

```
<210> SEQ ID NO 19
<211> LENGTH: 214
<212> TYPE: PRT
<213> ORGANISM: Artificial Sequence
<220> FEATURE:
<223> OTHER INFORMATION: light chain of monoclonal anti-CD147 antibody

<400> SEQUENCE: 19

Ser Ile Val Met Thr Gln Thr Pro Thr Phe Leu Val Val Ser Ala Gly
1               5                   10                  15

Asp Arg Val Thr Ile Thr Cys Lys Ala Ser Gln Ser Val Ile Asn Asp
            20                  25                  30

Val Ala Trp Tyr Gln Gln Lys Pro Gly Gln Ser Pro Lys Leu Leu Ile
        35                  40                  45

Phe Tyr Ala Ser Asn Arg Asn Thr Gly Val Pro Asp Arg Phe Thr Gly
50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Pro Pro Phe
                85                  90                  95

Thr Phe Gly Ser Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 20
<211> LENGTH: 230
<212> TYPE: PRT
<213> ORGANISM: Artificial Sequence
<220> FEATURE:
<223> OTHER INFORMATION: light chain of monoclonal anti-CD147 antibody

<400> SEQUENCE: 20

Met Gly Trp Ser Cys Ile Ile Leu Phe Leu Val Ala Thr Ala Thr Gly
1               5                   10                  15

Ser Ile Val Met Thr Gln Thr Pro Thr Phe Leu Val Val Ser Ala Gly
            20                  25                  30

Asp Arg Val Thr Ile Thr Cys Lys Ala Ser Gln Ser Val Ile Asn Asp
        35                  40                  45

Val Ala Trp Tyr Gln Gln Lys Pro Gly Gln Ser Pro Lys Leu Leu Ile
50                  55                  60

Phe Tyr Ala Ser Asn Arg Asn Thr Gly Val Pro Asp Arg Phe Thr Gly
65                  70                  75                  80

Ser Gly Tyr Gly Thr Asp Phe Thr Phe Thr Ile Ser Thr Val Gln Ala
                85                  90                  95
```

```
Glu Asp Leu Ala Val Tyr Phe Cys Gln Gln Asp Tyr Ser Pro Pro Phe
                100                 105                 110

Thr Phe Gly Ser Gly Thr Lys Leu Glu Ile Lys Arg Thr Val Ala Ala
            115                 120                 125

Pro Ser Val Phe Ile Phe Pro Pro Ser Asp Glu Gln Leu Lys Ser Gly
        130                 135                 140

Thr Ala Ser Val Val Cys Leu Leu Asn Asn Phe Tyr Pro Arg Glu Ala
145                 150                 155                 160

Lys Val Gln Trp Lys Val Asp Asn Ala Leu Gln Ser Gly Asn Ser Gln
                165                 170                 175

Glu Ser Val Thr Glu Gln Asp Ser Lys Asp Ser Thr Tyr Ser Leu Ser
            180                 185                 190

Ser Thr Leu Thr Leu Ser Lys Ala Asp Tyr Glu Lys His Lys Val Tyr
        195                 200                 205

Ala Cys Glu Val Thr His Gln Gly Leu Ser Ser Pro Val Thr Lys Ser
210                 215                 220

Phe Asn Arg Gly Glu Cys
225                 230

<210> SEQ ID NO 21
<211> LENGTH: 209
<212> TYPE: PRT
<213> ORGANISM: Artificial Sequence
<220> FEATURE:
<223> OTHER INFORMATION: light chain of monoclonal anti-CD147 antibody

<400> SEQUENCE: 21

Ser Ile Val Met Thr Gln Thr Pro Thr Phe Leu Val Val Ser Ala Gly
1               5                   10                  15

Asp Arg Val Thr Ile Thr Cys Lys Ala Ser Gln Ser Val Ile Asn Asp
            20                  25                  30

Val Ala Trp Tyr Gln Gln Lys Pro Gly Gln Ser Pro Lys Leu Leu Ile
        35                  40                  45

Phe Tyr Ala Ser Asn Arg Asn Thr Gly Val Pro Asp Arg Phe Thr Gly
    50                  55                  60

Ser Gly Tyr Gly Thr Asp Phe Thr Phe Thr Ile Ser Thr Val Gln Ala
65                  70                  75                  80

Glu Asp Leu Ala Val Tyr Phe Cys Gln Gln Asp Tyr Ser Pro Pro Phe
                85                  90                  95

Thr Phe Gly Ser Gly Thr Lys Thr Val Ala Ala Pro Ser Val Phe Ile
            100                 105                 110

Phe Pro Pro Ser Asp Glu Gln Leu Lys Ser Gly Thr Ala Ser Val Val
        115                 120                 125

Cys Leu Leu Asn Asn Phe Tyr Pro Arg Glu Ala Lys Val Gln Trp Lys
    130                 135                 140

Val Asp Asn Ala Leu Gln Ser Gly Asn Ser Gln Glu Ser Val Thr Glu
145                 150                 155                 160

Gln Asp Ser Lys Asp Ser Thr Tyr Ser Leu Ser Ser Thr Leu Thr Leu
                165                 170                 175

Ser Lys Ala Asp Tyr Glu Lys His Lys Val Tyr Ala Cys Glu Val Thr
            180                 185                 190

His Gln Gly Leu Ser Ser Pro Val Thr Lys Ser Phe Asn Arg Gly Glu
        195                 200                 205

Cys
```

```
<210> SEQ ID NO 22
<211> LENGTH: 225
<212> TYPE: PRT
<213> ORGANISM: Artificial Sequence
<220> FEATURE:
<223> OTHER INFORMATION: light chain of monoclonal anti-CD147 antibody

<400> SEQUENCE: 22

Met Gly Trp Ser Cys Ile Ile Leu Phe Leu Val Ala Thr Ala Thr Gly
1               5                   10                  15

Ser Ile Val Met Thr Gln Thr Pro Thr Phe Leu Val Val Ser Ala Gly
            20                  25                  30

Asp Arg Val Thr Ile Thr Cys Lys Ala Ser Gln Ser Val Ile Asn Asp
        35                  40                  45

Val Ala Trp Tyr Gln Gln Lys Pro Gly Gln Ser Pro Lys Leu Leu Ile
    50                  55                  60

Phe Tyr Ala Ser Asn Arg Asn Thr Gly Val Pro Asp Arg Phe Thr Gly
65                  70                  75                  80

Ser Gly Tyr Gly Thr Asp Phe Thr Phe Thr Ile Ser Thr Val Gln Ala
                85                  90                  95

Glu Asp Leu Ala Val Tyr Phe Cys Gln Gln Asp Tyr Ser Pro Pro Phe
            100                 105                 110

Thr Phe Gly Ser Gly Thr Lys Thr Val Ala Ala Pro Ser Val Phe Ile
        115                 120                 125

Phe Pro Pro Ser Asp Glu Gln Leu Lys Ser Gly Thr Ala Ser Val Val
    130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

Ser Lys Ala Asp Tyr Glu Lys His Lys Val Tyr Ala Cys Glu Val Thr
        195                 200                 205

His Gln Gly Leu Ser Ser Pro Val Thr Lys Ser Phe Asn Arg Gly Glu
    210                 215                 220

Cys
225
```

PHARMACEUTICAL PREPARATION STABLY COMPRISING CD147 MONOCLONAL ANTIBODY

FIELD OF THE INVENTION

The present disclosure relates to pharmaceutical formulations, in particular the stable pharmaceutical formulations comprising a monoclonal anti-CD147 antibody. The present disclosure also relates to the methods for preparing the pharmaceutical formulations and uses thereof.

BACKGROUND

Researches indicated that the CD147 molecule medicates a variety of biological functions in the process of tumor growth: (1) promoting the formation, spreading, and adhesion of pseudopodia in tumor cells; (2) promoting the movement of tumor cells; (3) promoting the VEGF expression in tumor endothelial cells and tumor neovascularization; (4) affecting the expression of downstream molecules; (5) inhibiting the tumor cell apoptosis induced by endoplasmic reticulum stress and the decreased chemo sensitivity; (6) affecting the formation of EMT via the signal pathway of TGF-β1-slug; (7) involving in the activation of T cells and formation of immune synapse; (8) promoting the invasion and metastasis of tumor cells (Zhang D W et al., J Hepatol. 2012; Chen Y K et al., PLoS One, 7(7), 2012; Tang J et al., Cell Death Differ, 19(11), 2012; Li Y et al., J Biol Chem, 287(7), 2012; Wu J et al., Oncogene, 2011; Zhao P et al., Hepatology, 54(6), 2011; Zhao P et al., Cancer Sci. 101(2), 2010; Gou X C et al., Cancer Sci. 100(5), 2009; Chen Y K et al., Cancer Letters, 278(1), 2009). Therefore, the CD147 molecule has become the new target for tumor treatment.

The occurrence, development, invasion and metastasis of tumors can be effectively controlled by using specific monoclonal antibodies for blocking the function of CD147 target. Because antibody molecules have a complex multilevel structure and are easily physically stick together, which may lead to an undesired immunological reactions or may block the syringes or pumps during administration to render them unsafe to patients, a long appreciated problem with liquid formulation of antibodies is the instability caused by aggregation.

Therefore, there is a need for pharmaceutical formulations of monoclonal anti-CD147 antibody having stability and quality consistency.

BRIEF SUMMARY OF THE INVENTION

The present disclosure provides stable pharmaceutical formulations comprising a monoclonal anti-CD147 antibody, which remain uniform and stable over a long period.

In one aspect, the present disclosure provides a pharmaceutical formulation comprising a monoclonal anti-CD147 antibody, a buffer, a protein protective agent and a surfactant.

In some embodiments, the monoclonal anti-CD147 antibody in the pharmaceutical formulation may comprise a heavy chain variable region and/or a light chain variable region, and the heavy chain variable region may comprise the CDR sequences shown below:
a CDR1 comprising the amino acid sequence of SEQ ID NO: 1;
a CDR2 comprising the amino acid sequence of SEQ ID NO: 2; and
a CDR3 comprising the amino acid sequence of SEQ ID NO: 3;
and the light chain variable region may comprise the CDR sequences shown below:
a CDR1 comprising the amino acid sequence of SEQ ID NO: 4;
a CDR2 comprising the amino acid sequence of SEQ ID NO: 5; and
a CDR3 comprising the amino acid sequence of SEQ ID NO: 6.

In some embodiments, the monoclonal anti-CD147 antibody can be a human murine chimeric monoclonal anti-CD147 antibody.

In some embodiments, the heavy chain variable region of the monoclonal anti-CD147 antibody may comprise the amino acid sequence of SEQ ID NO: 7, SEQ ID NO: 8, SEQ ID NO: 9 or SEQ ID NO: 10.

In some embodiments, the light chain variable region of the monoclonal anti-CD147 antibody may comprise the amino acid sequence of SEQ ID NO: 11, SEQ ID NO: 12, SEQ ID NO: 13 or SEQ ID NO: 14.

In some embodiments, the monoclonal anti-CD147 antibody may comprise a heavy chain comprising the amino acid sequence of SEQ ID NO: 15, SEQ ID NO: 16, SEQ ID NO: 17, or SEQ ID NO: 18 and/or a light chain comprising the amino acid sequence of SEQ ID NO: 19, SEQ ID NO: 20, SEQ ID NO: 21, or SEQ ID NO: 22.

In some embodiments, the monoclonal anti-CD147 antibody is a monoclonal HcHAb18 antibody comprising a heavy chain comprising the amino acid sequence of SEQ ID NO: 15 and a light chain comprising the amino acid sequence of SEQ ID NO: 19.

In some embodiments, the pharmaceutical formulation may have a pH of 5.0-8.0. For example, the pharmaceutical formulation may have a pH of 5.0-6.0, 6.0-7.0, or 7.0-8.0.

In some embodiments, the concentration of the monoclonal anti-CD147 antibody in the pharmaceutical formulation may be 1-40 mg/ml. For example, the concentration of the monoclonal anti-CD147 antibody in the pharmaceutical formulation may be 1-15 mg/ml, 15-25 mg/ml or 25-40 mg/ml.

In some embodiments, the buffer in the pharmaceutical formulation may be selected from one or more of a succinate buffer, a histidine buffer, a citrate buffer and an acetate buffer.

In some embodiments, the concentration of the buffer may be 5-50 mmol/L. For example, the concentration of the buffer may be 5-11 mmol/L, 11-25 mmol/L or 25-50 mmol/L.

In some embodiments, the pharmaceutical formulation has a pH of 5.0-6.0, and the buffer is a succinate buffer at a concentration of 11-25 mmol/L.

In some embodiments, the protein protective agent in the pharmaceutical formulation may be selected from one or more of sucrose and trehalose.

In some embodiments, the pharmaceutical formulation does not comprise an alcoholic protein protective agent.

In some embodiments, the concentration of the protein protective agent in the pharmaceutical formulation may be 10-200 mg/ml. For example, the concentration of the protein protective agent in the pharmaceutical formulation may be 10-70 mg/ml, 70-80 mg/ml, or 80-200 mg/ml.

In some embodiments, the protein protective agent may be trehalose and the concentration of trehalose in the pharmaceutical formulation is 70-80 mg/ml.

In some embodiments, the surfactant may be selected from one or more of polysorbate 20 and polysorbate 80.

In some embodiments, the concentration of the surfactant in the pharmaceutical formulation is 0.2-0.8 mg/ml. For example, the concentration of the surfactant in the pharmaceutical formulation is 0.2-0.35 mg/ml, 0.35-0.45 mg/ml or 0.45-0.8 mg/ml.

In some embodiments, the surfactant can be polysorbate 20 and the concentration of polysorbate 20 in the pharmaceutical formulation is 0.35-0.45 mg/ml.

In some embodiments, the concentration of the monoclonal anti-CD147 antibody in the pharmaceutical formulation is 15-25 mg/ml; the buffer is a succinate buffer and the concentration of the succinate buffer is 11-25 mmol/L; the protein protective agent is trehalose and the concentration of the trehalose in the pharmaceutical formulation is 70-80 mg/ml; the surfactant is polysorbate 20 and the concentration of polysorbate 20 in the pharmaceutical formulation is 0.35-0.45 mg/ml; and the pharmaceutical formulation has a pH of 5.0-6.0.

In some embodiments, the pharmaceutical formulation is stable at low temperature condition for at least 6 months. In some embodiments, the temperature of said low temperature condition is 2-8° C.

In some embodiments, the pharmaceutical formulation can be diluted 30-50 times by a diluent and remains stable at the temperature of 25±2° C. for at least 8 hours.

In some embodiments, the diluent is 0.9% NaCl injection.

In some embodiments, the pharmaceutical formulation remains stable for up to 10 days at an illumination of not less than 4500 lux and at a temperature of 2-8° C.

In some embodiments, the pharmaceutical formulation is an injection.

In another aspect, the present disclosure provides a use of the pharmaceutical formulation in the manufacture of a medicament for the treatment of CD147-associated diseases.

In some embodiments, the CD147-associated disease is non-small cell lung cancer.

In another aspect, the present disclosure provides a method of preparing the pharmaceutical formulation, comprising:
1) solution preparation:
   a) preparing an ultrafiltration buffer at a concentration of 5-25 mmol/L;
   b) preparing a first formulation solvent comprising a buffer, a protein protective agent and a surfactant, wherein the concentration of the buffer in the first formulation solvent is 5-50 mmol/L, the concentration of the protein protective agent in the first formulation solvent is 60-1200 mmol/L, and the concentration of the surfactant in the first formulation solvent is 1.2-4.8 mg/ml;
   c) preparing a second formulation solvent comprising a buffer, a protein protective agent and a surfactant, wherein the concentration of the buffer in the second formulation solvent is 5-50 mmol/L, the concentration of the protein protective agent in the second formulation solvent is 10-200 mmol/L and the concentration of the surfactant in the second formulation solvent is 0.2-0.8 mg/ml;
2) concentrating bulk of monoclonal anti-CD147 antibody to obtain a first solution of monoclonal anti-CD147 antibody having a concentration of monoclonal anti-CD147 antibody of 30-100 mg/ml;
3) injecting the first solution of monoclonal anti-CD147 antibody into an ultrafiltration system and conducting a continuous solvent exchange by six-fold volume using the ultrafiltration buffer to obtain a second solution of monoclonal anti-CD147 antibody;
4) adding the first formulation solvent into the second solution of monoclonal anti-CD147 antibody to obtain the pharmaceutical formulation having a concentration of monoclonal anti-CD147 antibody of 1-40 mg/ml.

In some embodiments, the method of the present disclosure further comprises:
5) adding the second formulation solvent into the pharmaceutical formulation obtained in above step 4) such that the concentration of the monoclonal anti-CD147 antibody reaches 15-25 mg/ml.

DETAILED DESCRIPTION OF THE INVENTION

Figure 1:
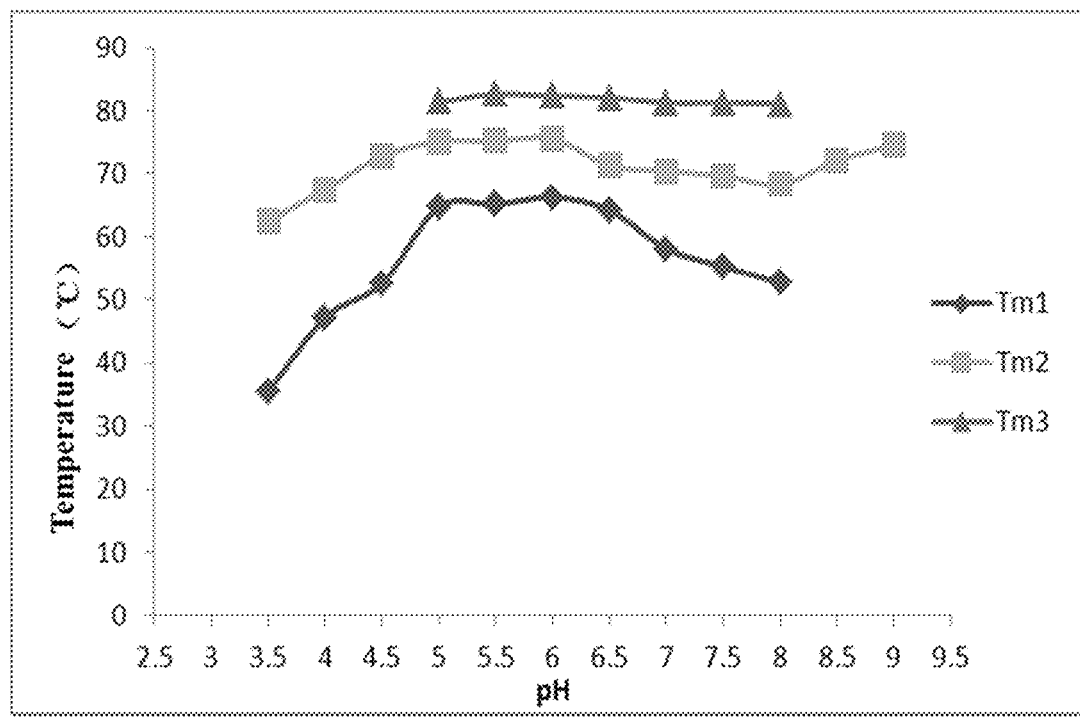
FIG. 1 shows the DSC scanning data of a monoclonal anti-CD147 antibody at different pH values.

The following description of the disclosure is merely intended to illustrate various embodiments of the present disclosure. The specific examples described should not be construed to limit the scope of the present disclosure. Various equivalents, variations, and modifications may be made by those of ordinary skilled in the art without departing from the spirit and scope of the present disclosure, and it is understood that the equivalents are also encompassed herein. All references cited herein, including publications, patents and patent applications are incorporated herein by reference in their entirety.

Antibody

As used herein, the term "monoclonal antibody" refers to a population of antibodies that comprises a homogeneous or substantially homogeneous single antibody. Monoclonal antibodies can be obtained from a single hybridoma cell clone (Milstein, C (1999). "The hybridoma revolution: an offshoot of basic research". *BioEssays*. 21 (11): 966-73). A complete monoclonal antibody comprises two heavy chains and two light chains. Each heavy chain consists of a heavy chain variable region ($V_H$) and a first, second, and third constant regions ($C_{H1}$, $C_{H2}$, $C_{H3}$). Each light chain consists of a light chain variable region ($V_L$) and a light chain constant region ($C_L$). Each of the $V_H$ and $V_L$ in heavy and light chains contains three complementarity determining regions (CDRs). The three CDRs are separated by contiguous portions known as framework regions (FRs), which are more highly conserved than the CDRs and form a scaffold to support the hypervariable loops. The six CDRs of one heavy chain and one light chain together constitute the antigen binding portion of the antibody and determine the specificity of the antibody. The monoclonal antibodies described herein also comprise fragments or derivatives of a complete monoclonal antibody that have an antigen binding function. The fragments or derivatives have the same antigen binding specificity as the complete monoclonal antibody, but the affinity of the fragments or derivatives for binding to their specific antigen may be the same as or different from that of the complete monoclonal antibody.

In some embodiments, the monoclonal antibody described herein comprises antigen-binding fragments. An antigen-binding fragment refers to one or more antibody fragments that retain the ability to specifically bind to an antigen. Examples of antigen-binding fragments include, without limitation, (i) a Fab fragment, which refers to a monovalent fragment composed of $V_L$, $V_H$, $C_L$, and $C_{H1}$ domains; (ii) a Fab' fragment, which refers to a Fab fragment that comprises a portion of the hinge region; (iii) a F(ab')$_2$ fragment, which refers to a bivalent fragment comprising two Fab fragments linked by a disulfide bond in the hinge region; (iv) a Fd fragment consisting of $V_H$ and $C_{H1}$ domains; (v) a Fv fragment consisting of the $V_L$ and $V_H$ domains of a single arm of the antibody; (vi) a dAb fragment (Ward et al., Nature 341:544-546 (1989); PCT Publication WO 90/05144) comprising a single variable domain; (vii) an isolated CDR; (viii) a single-chain Fv fragment, which refers to a monovalent fragment formed from the $V_L$ and $V_H$ domains that are linked directly or linked via a peptide chain (Huston J S et al., Proc Natl Acad Sci USA, 85:5879 (1988)).

In some embodiments, the monoclonal antibody described herein comprise a chimeric monoclonal antibody in which a portion of the heavy chain and/or light chain is identical or homologous with a corresponding sequence of antibodies derived from a particular species or belonging to a particular antibody class or subclass, and the rest chain is identical or homologous with a corresponding sequence of antibodies and the fragments thereof deriving from the other species or belonging to the other antibody class or subclass, as long as they exhibit the desired functional activity.

In some embodiments, the monoclonal antibodies described herein include human murine chimeric monoclonal antibodies having murine heavy chain and light chain variable regions, and human heavy chain and light chain constant regions.

In some embodiments, the monoclonal antibodies described herein include humanized monoclonal antibodies. A humanized form of a non-human (e.g., murine) antibody is a chimeric immunoglobulin, immunoglobulin chain or fragment thereof (e.g., Fv, Fab, Fab', F(ab')$_2$ or other antigen-binding sequences of the antibody) containing minimal sequences obtained from non-human immunoglobulin. In some examples, the humanized antibody may be a CDR-grafted antibody in which the amino acid sequence of a human CDR is introduced into the amino acid sequences of non-human $V_H$ and $V_L$ to replace the amino acid sequence of the corresponding non-human CDR. In other examples, most of the amino acid sequences of humanized antibodies may be derived from human immunoglobulins (receptor antibodies) where the amino acid residues of the CDRs of the receptor are replaced by the amino acid residues of the CDRs of non-human (e.g., mouse, rat, rabbit) antibody having the desired specificity, affinity and ability. In general, humanized antibodies comprise essentially at least one, and generally two variable domains, wherein all or substantially all of the CDR regions correspond to the sequence of a non-human immunoglobulin, and all or substantially all of the framework (FR) region is the sequence of human immunoglobulin. In some examples, the framework region residues of the variable regions of human immunoglobulins are replaced by the corresponding non-human residues. Moreover, a humanized antibody can comprise residues that are not found in either the receptor antibody or the imported CDR or framework region sequences.

The monoclonal anti-CD147 antibody described herein refers to a monoclonal antibody that specifically binds to the CD147 protein.

The CD147 protein described herein refers to a single transmembrane glycoprotein belonging to the immunoglobulin superfamily. Its full-length sequence has 269 amino acid residues, and the first 21 amino acid residues starting from the N-terminus are signal peptides, the amino acid residues 22-205 constitute the extracellular domain, the amino acid residues 206-229 constitute the transmembrane domain having a typical leucine zipper structure, and the amino acid residues 230-269 near the C-terminus constitute the intracellular domain. The four extracellular cysteines form two disulfide bonds, thereby constituting two Ig-like domains. A representative sequence of the CD147 protein may be, for example, as shown in GenBank No. BAC76828.1. Reference may also be made to, for example, Zhang D W et al., J Hepatol. 2012; Chen Y K et al., PLoS One, 7(7), 2012; Tang J et al., Cell Death Differ, 19(11), 2012; Li Y et al., J Biol Chem, 287(7), 2012; Wu J et al., Oncogene, 2011; Zhao P et al., Hepatology, 54 (6), 2011; Zhao P et al., Cancer Sci. 101(2), 2010; Gou X C et al., Cancer Sci. 100(5), 2009; Chen Y K et al., Cancer Letters, 278(1), 2009.

In some embodiments, the CD147 monoclonal antibodies described herein comprise heavy chain CDR sequences selected from the amino acid sequences of SEQ ID NOs: 1, 2 and 3. In some embodiments, the CD147 monoclonal antibodies described herein comprise light chain CDR sequences selected from the amino acid sequences of SEQ ID NO: 4, 5 and 6.

In some embodiments, the monoclonal anti-CD147 antibody described herein comprises a heavy chain variable region $V_H$ comprising the heavy chain CDR sequences of: CDR1 comprising the amino acid sequence of SEQ ID NO: 1, CDR2 comprising the amino acid sequence of SEQ ID NO: 2, and/or CDR3 comprising the amino acid sequence of SEQ ID NO:3.

In some embodiments, the monoclonal anti-CD147 antibody described herein comprises a light chain variable region $V_L$ comprising the light chain CDR sequences of: CDR1 comprising the amino acid sequence of SEQ ID NO: 4, CDR2 comprising the amino acid sequence of SEQ ID NO: 5, and/or CDR3 comprising the amino acid sequence of SEQ ID NO:6.

In some embodiments, the monoclonal anti-CD147 antibody described herein comprises a heavy chain variable region $V_H$ and a light chain variable region $V_L$. The heavy chain variable region $V_H$ comprises CDR1 comprising the amino acid sequence of SEQ ID NO: 1, CDR2 comprising the amino acid sequence of SEQ ID NO: 2, and/or CDR3 comprising the amino acid sequence of SEQ ID NO:3. The light chain variable region $V_L$ comprises CDR1 comprising the amino acid sequence of SEQ ID NO: 4, CDR2 comprising the amino acid sequence of SEQ ID NO: 5, and/or CDR3 comprising the amino acid sequence of SEQ ID NO: 6.

In some embodiments, the monoclonal anti-CD147 antibody described herein comprises a heavy chain variable region $V_H$ comprising the amino acid sequence of SEQ ID NO: 7, SEQ ID NO: 8, SEQ ID NO: 9, or SEQ ID NO: 10. In some embodiments, the monoclonal anti-CD147 antibody described herein comprises a light chain variable region $V_L$ comprising the amino acid sequence of SEQ ID NO: 11, SEQ ID NO: 12, SEQ ID NO: 13, or SEQ ID NO: 14. In some embodiments, the monoclonal anti-CD147 antibody described herein comprises a heavy chain variable region $V_H$ comprising the amino acid sequence of SEQ ID NO: 7, SEQ ID NO: 8, SEQ ID NO: 9, or SEQ ID NO: 10 and a light chain variable region $V_L$ comprising the amino acid sequence of SEQ ID NO: 11, SEQ ID NO: 12, SEQ ID NO: 13, or SEQ ID NO: 14. In some embodiments, the monoclonal anti-CD147 antibody described herein comprises a heavy chain variable region $V_H$ comprising the amino acid sequence of SEQ ID NO: 7 and a light chain variable region $V_L$ comprising the amino acid sequence of SEQ ID NO: 11.

In some embodiments, the monoclonal anti-CD147 antibody described herein further comprises an immunoglobulin constant region. In some embodiments, the immunoglobulin constant region comprises a heavy chain constant region and/or a light chain constant region. The heavy chain constant region comprises $C_{H1}$, $C_{H1}$-$C_{H2}$, or $C_{H1}$-$C_{H3}$ region, and the light chain constant region comprises a $C_L$ region.

In some embodiments, the monoclonal anti-CD147 antibody described herein includes a chimeric monoclonal anti-CD147 antibody, particularly human murine chimeric monoclonal anti-CD147 antibody.

In some embodiments, the human murine chimeric monoclonal anti-CD147 antibody described herein comprises a heavy chain comprising the amino acid sequence of SEQ ID NO: 15, SEQ ID NO: 16, SEQ ID NO: 17, or SEQ ID NO: 18. In some embodiments, the human murine chimeric monoclonal anti-CD147 antibody described herein comprises a light chain comprising the amino acid sequence of SEQ ID NO: 19, SEQ ID NO: 20, SEQ ID NO: 21, or SEQ ID NO: 22. In some embodiments, the human murine chimeric monoclonal anti-CD147 antibody described herein comprises a heavy chain comprising the amino acid sequence of SEQ ID NO: 15, SEQ ID NO: 16, SEQ ID NO: 17, or SEQ ID NO: 18 and a light chain comprising the amino acid sequence of SEQ ID NO: 19, SEQ ID NO: 20, SEQ ID NO: 21, or SEQ ID NO: 22.

In some embodiments, the monoclonal anti-CD147 antibody described herein is a monoclonal HcHAb18 antibody that comprises a heavy chain comprising the amino acid sequence of SEQ ID NO: 15 and a light chain comprising the amino acid sequence of SEQ ID NO: 19.

Exemplary amino acid sequences in some embodiments are listed in Table 1 below:

TABLE 1

Exemplary Amino Acid Sequences

| SEQ ID NO. | Amino Acid Sequence |
|---|---|
| 1 | GFTFSDAWMD |
| 2 | EIRSKANNHAPYYTESVKG |
| 3 | RDSTATH |
| 4 | KASQSVINDVA |
| 5 | YASNRNT |
| 6 | QQDYSPPFT |
| 7 | EVKLEESGGGLVQPGGSMKLSCVASGFTFSDAWMDWVRQSPEKGL EWVAEIRSKANNHAPYYTESVKGRFTISRDDSKSIIYLQMNNLRA EDTGIYYCTRDSTATHWGQGTLVTVSA |

TABLE 1-continued

Exemplary Amino Acid Sequences

| SEQ ID NO. | Amino Acid Sequence |
|---|---|
| 8 | MGWSCIILFLVATATGEVKLEESGGGLVQPGGSMKLSCVASGFTF SDAWMDWVRQSPEKGLEWVAEIRSKANNHAPYYTESVKGRFTISR DDSKSIIYLQMNNLRAEDTGIYYCTRDSTATHWGQGTLVTVSA |
| 9 | EVKLEESGGGLVQPGGSMKLSCVASGFTFSDAWMDWVRQSPEKGL EWVAEIRSKANNHAPYYTESVKGRFTISRDDSKSIIYLQMNNLRA EDTGIYYCTRDSTATHWGQGT |
| 10 | MGWSCIILFLVATATGEVKLEESGGGLVQPGGSMKLSCVASGFTF SDAWMDWVRQSPEKGLEWVAEIRSKANNHAPYYTESVKGRFTISR DDSKSIIYLQMNNLRAEDTGIYYCTRDSTATHWGQGT |
| 11 | SIVMTQTPTFLVVSAGDRVTITCKASQSVINDVAWYQQKPGQSPK LLIFYASNRNTGVPDRFTGSGYGTDFTFTISTVQAEDLAVYFCQQ DYSPPFTFGSGTKLEIKR |
| 12 | MGWSCIILFLVATATGSIVMTQTPTFLVVSAGDRVTITCKASQSV INDVAWYQQKPGQSPKLLIFYASNRNTGVPDRFTGSGYGTDFTFT ISTVQAEDLAVYFCQQDYSPPFTFGSGTKLEIKR |
| 13 | SIVMTQTPTFLVVSAGDRVTITCKASQSVINDVAWYQQKPGQSPK LLIFYASNRNTGVPDRFTGSGYGTDFTFTISTVQAEDLAVYFCQQ DYSPPFTFGSGTK |
| 14 | MGWSCIILFLVATATGSIVMTQTPTFLVVSAGDRVTITCKASQSV INDVAWYQQKPGQSPKLLIFYASNRNTGVPDRFTGSGYGTDFTFT ISTVQAEDLAVYFCQQDYSPPFTFGSGTK |
| 15 | EVKLEESGGGLVQPGGSMKLSCVASGFTFSDAWMDWVRQSPEKGL EWVAEIRSKANNHAPYYTESVKGRFTISRDDSKSIIYLQMNNLRA EDTGIYYCTRDSTATHWGQGTLVTVSAASTKGPSVFPLAPSSKST SGGTAALGCLVKDYFPEPVTVSWNSGALTSGVHTFPAVLQSSGLY SLSSVVTVPSSSLGTQTYICNVNHKPSNTKVDKRVEPKSCDKTHT CPPCPAPELLGGPSVFLFPPKPKDTLMISRTPEVTCVVVDVSHED PEVKFNWYVDGVEVHNAKTKPREEQYNSTYRVVSVLTVLHQDWLN GKEYKCKVSNKALPAPIEKTISKAKGQPREPQVYTLPPSRDELTK NQVSLTCLVKGFYPSDIAVEWESNGQPENNYKTTPPVLDSDGSFF LYSKLTVDKSRWQQGNVFSCSVMHEALHNHYTQKSLSLSPGK |
| 16 | MGWSCIILFLVATATGEVKLEESGGGLVQPGGSMKLSCVASGFTF SDAWMDWVRQSPEKGLEWVAEIRSKANNHAPYYTESVKGRFTISR DDSKSIIYLQMNNLRAEDTGIYYCTRDSTATHWGQGTLVTVSAAS TKGPSVFPLAPSSKSTSGGTAALGCLVKDYFPEPVTVSWNSGALT SGVHTFPAVLQSSGLYSLSSVVTVPSSSLGTQTYICNVNHKPSNT KVDKRVEPKSCDKTHTCPPCPAPELLGGPSVFLFPPKPKDTLMIS RTPEVTCVVVDVSHEDPEVKFNWYVDGVEVHNAKTKPREEQYNST YRVVSVLTVLHQDWLNGKEYKCKVSNKALPAPIEKTISKAKGQPR EPQVYTLPPSRDELTKNQVSLTCLVKGFYPSDIAVEWESNGQPEN NYKTTPPVLDSDGSFFLYSKLTVDKSRWQQGNVFSCSVMHEALHN HYTQKSLSLSPGK |
| 17 | EVKLEESGGGLVQPGGSMKLSCVASGFTFSDAWMDWVRQSPEKGL EWVAEIRSKANNHAPYYTESVKGRFTISRDDSKSIIYLQMNNLRA EDTGIYYCTRDSTATHWGQGTASTKGPSVFPLAPSSKSTSGGTAA LGCLVKDYFPEPVTVSWNSGALTSGVHTFPAVLQSSGLYSLSSVV TVPSSSLGTQTYICNVNHKPSNTKVDKRVEPKSCDKTHTCPPCPA PELLGGPSVFLFPPKPKDTLMISRTPEVTCVVVDVSHEDPEVKFN WYVDGVEVHNAKTKPREEQYNSTYRVVSVLTVLHQDWLNGKEYKC KVSNKALPAPIEKTISKAKGQPREPQVYTLPPSRDELTKNQVSLT CLVKGFYPSDIAVEWESNGQPENNYKTTPPVLDSDGSFFLYSKLT VDKSRWQQGNVFSCSVMHEALHNHYTQKSLSLSPGK |
| 18 | MGWSCIILFLVATATGEVKLEESGGGLVQPGGSMKLSCVASGFTF SDAWMDWVRQSPEKGLEWVAEIRSKANNHAPYYTESVKGRFTISR DDSKSIIYLQMNNLRAEDTGIYYCTRDSTATHWGQGTASTKGPSV FPLAPSSKSTSGGTAALGCLVKDYFPEPVTVSWNSGALTSGVHTF PAVLQSSGLYSLSSVVTVPSSSLGTQTYICNVNHKPSNTKVDKRV EPKSCDKTHTCPPCPAPELLGGPSVFLFPPKPKDTLMISRTPEVT CVVVDVSHEDPEVKFNWYVDGVEVHNAKTKPREEQYNSTYRVVSV LTVLHQDWLNGKEYKCKVSNKALPAPIEKTISKAKGQPREPQVYT LPPSRDELTKNQVSLTCLVKGFYPSDIAVEWESNGQPENNYKTTP PVLDSDGSFFLYSKLTVDKSRWQQGNVFSCSVMHEALHNHYTQKS LSLSPGK |

TABLE 1-continued

Exemplary Amino Acid Sequences

| SEQ ID NO. | Amino Acid Sequence |
|---|---|
| 19 | SIVMTQTPTFLVVSAGDRVTITCKASQSVINDVAWYQQKPGQSPK LLIFYASNRNTGVPDRFTGSGYGTDFTFTISTVQAEDLAVYFCQQ DYSPPFTFGSGTKLEIKRTVAAPSVFIFPPSDEQLKSGTASVVCL LNNFYPREAKVQWKVDNALQSGNSQESVTEQDSKDSTYSLSSTLT LSKADYEKHKVYACEVTHQGLSSPVTKSFNRGEC |
| 20 | MGWSCIILFLVATATGSIVMTQTPTFLVVSAGDRVTITCKASQSV INDVAWYQQKPGQSPKLLIFYASNRNTGVPDRFTGSGYGTDFTFT ISTVQAEDLAVYFCQQDYSPPFTFGSGTKLEIKRTVAAPSVFIFP PSDEQLKSGTASVVCLLNNFYPREAKVQWKVDNALQSGNSQESVT EQDSKDSTYSLSSTLTLSKADYEKHKVYACEVTHQGLSSPVTKSF NRGEC |
| 21 | SIVMTQTPTFLVVSAGDRVTITCKASQSVINDVAWYQQKPGQSPK LLIFYASNRNTGVPDRFTGSGYGTDFTFTISTVQAEDLAVYFCQQ DYSPPFTFGSGTKTVAAPSVFIFPPSDEQLKSGTASVVCLLNNFY PREAKVQWKVDNALQSGNSQESVTEQDSKDSTYSLSSTLTLSKAD YEKHKVYACEVTHQGLSSPVTKSFNRGEC |
| 22 | MGWSCIILFLVATATGSIVMTQTPTFLVVSAGDRVTITCKASQSV INDVAWYQQKPGQSPKLLIFYASNRNTGVPDRFTGSGYGTDFTFT ISTVQAEDLAVYFCQQDYSPPFTFGSGTKTVAAPSVFIFPPSDEQ LKSGTASVVCLLNNFYPREAKVQWKVDNALQSGNSQESVTEQDSK DSTYSLSSTLTLSKADYEKHKVYACEVTHQGLSSPVTKSFNRGEC |

The present disclosure relates to a pharmaceutical formulation comprising the monoclonal anti-CD147 antibody. In some embodiments, the pharmaceutical formulation of the present disclosure may comprise the monoclonal anti-CD147 antibody at a concentration range of 1-40 mg/ml. In some embodiments, the concentration of monoclonal anti-CD147 antibody is any concentration value within the above range. For example, according to the need, the concentration of the monoclonal anti-CD147 antibody in the pharmaceutical formulation may be at least 1 mg/ml, at least 2 mg/ml, at least 3 mg/ml, at least 4 mg/ml, at least 5 mg/ml, at least 6 mg/ml, at least 7 mg/ml, at least 8 mg/ml, at least 9 mg/ml, at least 10 mg/ml, at least 11 mg/ml, at least 12 mg/ml, at least 13 mg/ml, at least 14 mg/ml, at least 15 mg/ml, at least 16 mg/ml, at least 17 mg/ml, at least 18 mg/ml, at least 19 mg/ml, at least 20 mg/ml, at least 21 mg/ml, at least 22 mg/ml, at least 23 mg/ml, at least 24 mg/ml, or at least 25 mg/ml, and at most 40 mg/ml, at most 39 mg/ml, at most 38 mg/ml, at most 37 mg/ml, at most 36 mg/ml, at most 35 mg/ml, at most 34 mg/ml, at most 33 mg/ml, at most 32 mg/ml, at most 31 mg/ml, at most 30 mg/ml, at most 29 mg/ml, at most 28 mg/ml, at most 27 mg, at most 26 mg/ml, at most 25 mg/ml, at most 24 mg/ml, at most 23 mg/ml, at most 22 mg/ml, at most 21 mg/ml, at most 20 mg/ml, at most 19 mg/ml, at most 18 mg/ml, at most 17 mg/ml, at most 16 mg/ml, or at most 15 mg/ml.

In some embodiments, the pharmaceutical formulation of the present disclosure may comprise the monoclonal anti-CD147 antibody at a concentration of 15-25 mg/ml. In some embodiments, the concentration of the monoclonal anti-CD147 antibody may be 15-24 mg/ml, 15-23 mg/ml, 15-22 mg/ml, 15-21 mg/ml, 16-21 mg/ml, 17-21 mg/ml, 18-21 mg/ml, or 19-21 mg/ml.

Buffers

The term "buffer" refers to a buffered solution that resists changes in pH by the action of its acid-base conjugate components. The "buffer" used herein refers to a solution of a compound which is known to be safe when used in a pharmaceutical formulation and maintains or controls the pH of the formulation in a desired range. Acceptable buffers capable of controlling the pH in a range from mild acidic pH to mild alkaline pH (e.g. pH 5.0-8.0) include, but are not limited to, one or any combination of phosphate buffer, acetate buffer, citrate buffer, arginine buffer, 2-amino-2-hydroxymethyl-1,3-propanediol (TRIS) buffer, histidine buffer and the like.

The stable pharmaceutical formulation of the present disclosure may comprise a buffer that allows the pharmaceutical formulation to have a pH of 5.0-8.0, such as a pH of 5.0-6.0, 6.0-7.0, or 7.0-8.0. In some embodiments, suitable buffers allow the pharmaceutical formulations of the present disclosure to have a pH of 5.0-6.0. In particular, the pH of the pharmaceutical formulation of the present disclosure may be any pH value in the pH ranges listed above, such as 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9 or 8.0.

Examples of buffers that can control the pH of a pharmaceutical formulation within a desired range include succinate buffers, histidine buffers, citrate buffers, acetate buffers, and other organic or inorganic acid buffers. These buffers can be used alone, alternatively, two or more of these buffers may be used in combination. Preferably, the pharmaceutical formulation of the present disclosure comprises succinate buffer, histidine buffer, citrate buffer or acetate buffer. More preferably, the pharmaceutical formulation of the present disclosure comprises a succinate buffer.

The "succinate buffer" is a buffer comprising succinate ions. The succinate buffer may comprise one or more of succinic acid, monosodium succinate, disodium succinate, monopotassium succinate, dipotassium succinate, sodium chloride, and potassium chloride. In some embodiments, the succinate buffer can be a succinic acid-disodium succinate buffer. In some embodiments, the pH of the succinate buffer can be any pH value in the range of 5.0-6.0, such as 5.0, 5.1, 5.2, 5.3, 5.4, 5.5, 5.6, 5.7, 5.8, 5.9, or 6.0.

The "histidine buffer" is a buffer comprising histidine ions. The histidine buffer may comprise one or more of histidine, histidine hydrochloride, histidine acetate, histidine phosphate, histidine sulfate and the like. In some embodiments, the histidine buffer can be a histidine-histidine hydrochloride buffer. In some embodiments, the pH of the histidine buffer can be any pH value in the range of 5.0-6.0, such as 5.0, 5.1, 5.2, 5.3, 5.4, 5.5, 5.6, 5.7, 5.8, 5.9, or 6.0.

The "citrate buffer" is a buffer comprising citrate ions. The citrate buffer may comprise one or more of citric acid, monosodium citrate, disodium citrate, trisodium citrate, monopotassium citrate, dipotassium citrate, tripotassium citrate, sodium chloride, potassium chloride and the like. In some embodiments, the citrate buffer can be a citric acid-trisodium citrate buffer. In some embodiments, the pH of the citrate buffer can be any pH value in the range of 5.0-6.0, such as 5.0, 5.1, 5.2, 5.3, 5.4, 5.5, 5.6, 5.7, 5.8, 5.9, or 6.0.

The "acetate buffer" is a buffer comprising acetate ions. The acetate buffer may comprise one or more of acetic acid, potassium acetate, sodium acetate, sodium chloride, potassium chloride and the like. In some embodiments, the acetate buffer can be an acetic acid-sodium acetate buffer. In some embodiments, the pH of the acetate buffer may be any pH value in the range of 5.0-6.0, such as 5.0, 5.1, 5.2, 5.3, 5.4, 5.5, 5.6, 5.7, 5.8, 5.9, or 6.0.

The concentration of the buffer described herein refers to the concentration of buffer ions in the buffer. In some embodiments, the suitable concentration of buffers used in the pharmaceutical formulations of the present disclosure may be 5-50 mmol/L. In some embodiments, the concentration of the buffer is any concentration value within above range. For example, the concentration of the buffer may be at least 5 mmol/L, at least 6 mmol/L, at least 7 mmol/L, at least 8 mmol/L, at least 9 mmol/L, at least 10 mmol/L, at least 11 mmol/L, at least 12 mmol/L, at least 13 mmol/L, at least 14 mmol/L, at least 15 mmol/L, at least 16 mmol/L, at least 17 mmol/L, at least 18 mmol/L, at least 19 mmol/L, at least 20 mmol/L, at least 21 mmol/L, at least 22 mmol/L, at least 23 mmol/L, at least 24 mmol/L, at least 25 mmol/L, at least 30 mmol/L, at least 35 mmol/L, at least 40 mmol/L, or at least 45 mmol/L, and at most 50 mmol/L, at most 45 mmol/L, at most 40 mmol/L, at most 35 mmol/L, at most 30 mmol/L, at most 25 mmol/L, at most 24 mmol/L, at most 23 mmol/L, at most 22, at most 21 mmol/L, at most 20 mmol/L, at most 19 mmol/L, at most 18 mmol/L, at most 17 mmol/L, at most 16 mmol/L, at most 15 mmol/L, at most 14 mmol/L L, at most 13 mmol/L, at most 12 mmol/L, at most 11 mmol/L, at most 10 mmol/L, at most 9 mmol/L, at most 8 mmol/L, at most 7 mmol/L, or at most 6 mmol/L, depending on the specific buffer and the desired stability of the pharmaceutical formulation.

In some embodiments, the buffer for the pharmaceutical formulation of the present disclosure is a succinate buffer, including a succinic acid-disodium succinate buffer, at a concentration of 5-50 mmol/L. In some embodiments, the concentration of the succinate buffer may be 11-25 mmol/L, 12-25 mmol/L, 13-25 mmol/L, 14-25 mmol/L, 15-25 mmol/L, 16-25 mmol/L, 17-25 mmol/L, 18-25 mmol/L, 19-25 mmol/L, 20-25 mmol/L, 21-25 mmol/L, 22-25 mmol/L, or 23-25 mmol/L.

Protein Protective Agent

As used herein, the term "protein protective agent" refers to an agent that, when bound to a protein of interest, prevents or reduces the chemical and/or physical instability of the protein. Examples of the protein protective agent include sugars, alcohols, acids, salts, polymers and the like. Examples of sugars include glucose, sucrose, trehalose, lactose, dextran and the like. Examples of alcohols include sorbitol and the like. Examples of acids include citric acid, phosphoric acid, tartaric acid, amino acids, ethylene diamine tetraacetic acid and the like. Examples of salts include sodium sulfate, sodium glutamate, sodium chloride, potassium chloride, ammonium acetate and the like. Examples of polymers include polyethylene glycol, povidone and the like.

In some embodiments, the protein protective agent used in the pharmaceutical formulations of the present disclosure is selected from sugars. In some embodiments, the protein protective agent used in the pharmaceutical formulations of the present disclosure is selected from the group consisting of sucrose, trehalose or combinations thereof.

In some embodiments, the pharmaceutical formulations of the present disclosure do not comprise an alcoholic protein protective agent.

In some embodiments, the concentration of the protein protective agent used in the pharmaceutical formulation of the present disclosure may be 10-200 mg/ml in the pharmaceutical formulation. In some embodiments, the concentration of the protein protective agent is any value within above range. For example, the concentration of the protein protective agent in the pharmaceutical formulation may be at least 10 mg/ml, at least 20 mg/ml, at least 30 mg/ml, at least 40 mg/ml, at least 50 mg/ml, at least 60 mg/ml, at least 70 mg/ml, at least 80 mg/ml, at least 90 mg/ml, at least 100 mg/ml, or at least 110 mg/ml, and at most 200 mg/ml, at most 190 mg/ml, at most 180 mg/ml, at most 170 mg/ml, at most 160 mg/ml, at most 150 mg/ml, at most 140 mg/ml, at most 130 mg/ml, at most 120 mg/ml, at most 110 mg/ml, at most 100 mg/ml, at most 90 mg/ml, or at most 80 mg/ml, depending on the specific protein protective agent and the desired stability of pharmaceutical formulation.

In some embodiments, the protein protective agent used in the pharmaceutical formulation of the present disclosure is trehalose at a concentration of 10-200 mg/ml in the pharmaceutical formulation. In some embodiments, the concentration of trehalose in the pharmaceutical formulation may be 70-100 mg/ml, 70-95 mg/ml, 70-90 mg/ml, 70-85 mg/ml, or 70-80 mg/ml.

Surfactant

As used herein, the term "surfactant" refers to an organic material having an amphiphilic structure that is both hydrophilic and hydrophobic, i.e., it comprises groups having opposite solubility tendency, e.g., oil-soluble hydrocarbon chain and water-soluble ionic group. Surfactants can be classified into anionic, cationic and non-ionic surfactants depending on the charge of the surface active moiety.

Examples of surfactants include polysorbates (e.g., polysorbate 20 or 80), poloxamers (e.g., poloxamer 188), Triton, and polyethylene glycol, polypropylene glycol and copolymers of ethylene glycol and propylene glycol (e.g., Pluronics, PF68 etc.). In some embodiments, the surfactant of the pharmaceutical formulation of the present disclosure is selected from polysorbate 20, polysorbate 80 or combinations thereof.

In some embodiments, the concentration of the surfactant in the pharmaceutical formulation of the present disclosure may be 0.2-0.8 mg/ml. In some embodiments, the concentration of surfactant is any value within above range. For example, the concentration of the surfactant in the pharmaceutical formulation may be at least 0.2 mg/ml, at least 0.25 mg/ml, at least 0.3 mg/ml, at least 0.35 mg/ml, at least 0.4 mg/ml, at least 0.45 mg/ml, at least 0.5 mg/ml, at least 0.55 mg/ml, at least 0.6 mg/ml, at least 0.65 mg/ml, at least 0.7 mg/ml, or at least 0.75 mg/ml, and at most 0.8 mg/ml, at most 0.75 mg/ml, at most 0.7 mg/ml, at most 0.65 mg/ml, at most 0.6 mg/ml, at most 0.55 mg/ml, at most 0.5 mg/ml, at most 0.45 mg/ml, at most 0.4 mg/ml, at most 0.35 mg/ml, at most 0.3 mg/ml, or at most 0.25 mg/ml, depending on the specific surfactant and the desired stability of pharmaceutical formulation.

In some embodiments, the surfactant of the pharmaceutical formulation of the present disclosure is polysorbate 20 at a concentration of 0.2-0.8 mg/ml in the pharmaceutical formulation. In some embodiments, the concentration of polysorbate 20 in the pharmaceutical formulation can be 0.35-0.45 mg/ml, 0.36-0.45 mg/ml, 0.37-0.45 mg/ml, 0.38-0.45 mg/ml, 0.39-0.45 mg/ml, 0.39-0.44 mg/ml, 0.39-0.43 mg/ml, or 0.39-0.42 mg/ml.

Other Materials

The pharmaceutical formulations of the present disclosure can optionally further comprise other materials such as, but not limited to, isotonic agents, diluents and the like.

The term "isotonic agent" refers to a compound or composition that can impart a suitable osmotic tension to a drug to avoid the net flow of water across the cell membrane that contacts the drug. In some embodiments, the formulation of the present disclosure has substantially the same osmotic pressure as human blood. In some embodiments, the formulation of the present disclosure has an osmotic pressure of 300-350 mOsmol/kg. Suitable isotonic agents include, but are not limited to, glycerin, amino acids or proteins (e.g., glycine or albumin), salts (e.g., sodium chloride), and sugars (e.g., glucose, mannitol, sucrose and lactose).

The term "diluent" is pharmaceutically acceptable and can be used to dilute the pharmaceutical formulations of the present disclosure. Typical diluents include water, physiological saline, antibacterial agents for injection, pH buffer, sterile salt solution, Ringer solution, or glucose solution. In some embodiments, the diluent used in the present disclosure is 0.9% NaCl injection.

Formulation

In one aspect, the present disclosure provides a stable pharmaceutical formulation comprising a monoclonal anti-CD147 antibody, a buffer, a protein protective agent and a surfactant. The pharmaceutical formulation has a pH of 5.0-8.0, in some embodiments, a pH of 5.0-6.0, to achieve sufficient stability.

In some embodiments, the pharmaceutical formulation of the present disclosure comprises:
a monoclonal anti-CD147 antibody at a concentration of 15-25 mg/ml;
a buffer, preferably a succinate buffer, a histidine buffer, a citrate buffer or an acetate buffer, most preferably a succinate buffer, at a concentration of 5-50 mmol/L, preferably 11-25 mmol/L in the pharmaceutical formulation;
a protein protective agent, preferably sucrose or trehalose, most preferably trehalose, at a concentration of 10-200 mg/ml, preferably 70-80 mg/ml in the pharmaceutical formulation;
a surfactant, preferably polysorbate 80 or polysorbate 20, most preferably polysorbate 20, at a concentration of 0.2-0.8 mg/ml, preferably 0.35-0.45 mg/ml in the pharmaceutical formulation;
and wherein the pharmaceutical formulation has a pH of 5.0-6.0.

In some embodiments, the pharmaceutical formulation of the present disclosure comprises a monoclonal anti-CD147 antibody at a concentration of about 19-21 mg/ml, a succinate buffer at a concentration of about 23-25 mmol/L, trehalose at a concentration of about 70-80 mg/ml and polysorbate 20 at a concentration of about 0.35-0.45 mg/ml, wherein the pH of the pharmaceutical formulation is 5.5-5.8.

Chemical degradation or aggregation of antibody molecules to form higher-order polymers, deglycosylation, glycosylation, oxidation, or other structural modifications that may result in a decrease in at least one functional activity of the monomeric protein may cause instability of the antibody formulation. For the pharmaceutical formulation containing a monoclonal anti-CD147 antibody, the monoclonal anti-CD147 antibody may undergo chemical degradation during storage of the pharmaceutical formulation, resulting in a decrease in the concentration of the antibody. The monoclonal anti-CD147 antibody may also aggregate and form sometimes insoluble polymer in the form of a polymerized molecule comprising a plurality of antibody molecules, resulting in a decrease in the content of monomers comprising individual antibody molecule. Therefore, an increase in the content of polymeric antibodies will result in a decrease in the purity of the monomeric antibodies. Moreover, the turbidity of the pharmaceutical formulation may increase due to the formation of insoluble polymers.

In some embodiments, the pharmaceutical formulation comprising a monoclonal anti-CD147 antibody of the present disclosure can maintain stable over a long period of time, wherein the physical and/or chemical stability and/or functional activity of the monoclonal anti-CD147 antibody are maintained relatively constant over time. In some embodiments, the concentration of antibody protein, purity of protein, activity of protein, pH of the formulation, osmotic pressure of the formulation, appearance of the formulation, insoluble particles in the formulation, etc. may serve as indicators of the stability of the pharmaceutical formulation. Various analytical techniques for measuring protein stability are available in the art and are reviewed in *Peptide and Protein Drug Delivery*, 247-301, edited by Vincent Lee, Marcel Dekker Inc., New York, N.Y. Press (1991) and Jones, A. *Adv. Drug Delivery Rev.* 10: 29-90 (1993). In some embodiments, the stability of the pharmaceutical formulation can be measured by methods known in the art at a selected condition for a selected time period.

In some embodiments, the formulation may be subjected to tests of differential scanning calorimetry (DSC), accelerated thermal stability, light stability, freeze-thaw stability, oscillation stability, long-term stability, dilution stability, and/or high temperature stability. For example, in a DSC test, the thermal transition midpoint (Tm) of the antibody in the formulation is measured with differential scanning calorimeter. For example, in a freeze-thaw stability test, the pharmaceutical formulation can be subjected to three cycles, $-15\pm5°$ C. for 2 days and then $25\pm2°$ C. for 2 days in each cycle, and samples are taken at the 0, 4th, 8th and 12th day for measurement, alternatively, the pharmaceutical formulation can be subjected to five cycles, $-15\pm5°$ C. for 2 days and then $25\pm2°$ C. for 2 days in each cycle, and samples are taken at the 0, 4th and 20th day for measurement. For example, in an oscillation stability test, the pharmaceutical formulation can be oscillated at a rotation speed of 67 rpm at room temperature for 24 hours and samples are taken at the 0, 3rd, 6th and 24th hour for measurement. For example, in a light stability test, the pharmaceutical formulation can be stored at $5\pm3°$ C. under an illumination of $4500\pm500$ Lux for 10 days, and samples are taken at the 0, 5th and 10th day for measurement. For example, in a long-term stability test, the pharmaceutical formulation can be stored at 2-8° C. for 2 years, and samples are taken at the 0, 3rd, 6th, 9th, 12th, 18th and 24th month for measurement. For example, in a dilution stability test, the pharmaceutical formulation is diluted with 0.9% NaCl injection and is stored at $25\pm2°$ C. for 8 hours, and samples are taken at the 0, 0.5, 1st, 2nd, 4th and 8th hour for measurement. In a high temperature stability test, the pharmaceutical preparation can be stored at $40\pm2°$ C. for 10 days, and samples are taken at the 0th, 5th, and 10th day for measurement.

In some embodiments, a stable pharmaceutical formulation means that in the DSC test, the pharmaceutical formulation shows three Tm values of the monoclonal anti-CD147 antibody.

In some embodiments, a stable pharmaceutical formulation means that in the test of accelerated thermal stability, the decrease in protein purity for the pharmaceutical formulation is not more than 5.0%, not more than 4.0%, not more than 3.0%, not more than 2.0% or not more than 1.0%, wherein the protein purity can be measured by the CE-SDS method.

In some embodiments, a stable pharmaceutical formulation means that in the test of oscillation stability, the increase in polymer content for the pharmaceutical formulation is less than about 1%, less than about 0.9%, less than about 0.8%, less than about 0.7%, less than about 0.6%, less than about 0.5%, less than about 0.4%, less than about 0.3%, less than about 0.2%, or less than about 0.1%, wherein the polymer content can be measured by the SE-HPLC method.

In some embodiments, a stable pharmaceutical formulation means that in the test of freeze-thaw stability, the increase in polymer content for the pharmaceutical formulation is less than about 1.0%, less than about 0.9%, less than about 0.8%, less than about 0.7%, less than about 0.6%, or less than about 0.5%, wherein the polymer content can be measured by the SE-HPLC method.

In some embodiments, a stable pharmaceutical formulation means that in the tests of high temperature stability, light stability, freeze-thaw stability, long-term stability or dilution stability, the protein purity for the pharmaceutical formulation is 95.5% or more, 96% or more, 96.5% or more, 97% or more, 97.5% or more, 98% or more, 98.5% or more, 99% or more, or 99.5% or more, wherein the protein purity can be measured by the CE-SDS method.

In some embodiments, a stable pharmaceutical formulation means that in the tests of high temperature stability, light stability, freeze-thaw stability, long-term stability or dilution stability, less than about 10%, less than about 5%, less than about 4%, less than about 3%, less than about 2%, or less than about 1% of proteins in the pharmaceutical formulation are polymers, wherein the polymer content can be measured by the SE-HPLC method.

In some embodiments, a stable pharmaceutical formulation means that in the test of dilution stability, the amount of insoluble particles having a particle size of 10 μm or more in the pharmaceutical formulation is ≤6000 particles/ml, ≤5000 particles/ml, ≤4000 particles/ml, ≤3000 particles/ml, ≤2000 particles/ml, ≤1000 particles/ml, ≤900 particles/ml, ≤800 particles/ml, ≤700 particles/ml, ≤600 particles/ml, ≤500 particles/ml, ≤400 particles/ml, ≤300 particles/ml, ≤200 particles/ml, ≤100 particles/ml, ≤90 particles/ml, ≤80 particles/ml, or ≤70 particles/ml; the amount of insoluble particles having a particle size of 25 μm or more is ≤600 particles/ml, ≤500 particles/ml, ≤400 particles/ml, ≤300 particles/ml, ≤200 particles/ml, ≤100 particles/ml, ≤90 particles/ml, ≤80 particles/ml, ≤70 particles/ml, ≤60 particles/ml, ≤50 particles/ml, ≤40 particles/ml, ≤30 particles/ml, ≤20 particles/ml, ≤10 particles/ml, ≤9 particles/ml, ≤8 particles/ml, ≤7 particles/ml, ≤6 particles/ml, ≤5 particles/ml, ≤4 particles/ml, ≤3 particles/ml, ≤2 particles/ml, or ≤1 particles/ml, wherein the amount of insoluble particles was measured by "insoluble particle inspection method" according to Preparation General Principle 0903 of Part III of the Chinese Pharmacopoeia (2010 edition).

In some embodiments, a stable pharmaceutical formulation means that in the tests of high temperature stability, light stability, freeze-thaw stability, long-term stability or dilution stability, the change of protein concentration for the pharmaceutical formulation is not more than +/−5%, not more than +/−4%, not more than +/−3%, not more than +/−2%, not more than +/−1%, or not more than +/−0.5%, wherein the protein concentration can be measured by UV-vis spectrophotometry according to the General Principle 0401 of Part III of Chinese Pharmacopoeia (2010 edition).

In some embodiments, a stable pharmaceutical formulation means that in the tests of high temperature stability, light stability, freeze-thaw stability, long-term stability or dilution stability, the functional activity of the pharmaceutical formulation is 50%-150%, wherein "functional activity" refers to the ability of the pharmaceutical formulation to kill or inhibit a specific target cell, and can be measured by the cytotoxicity test. The functional activity of the pharmaceutical formulation can be quantitatively described, wherein the target cell killing activity of a fresh pharmaceutical formulation sample (reference sample) is defined as 100%, and the functional activity of a pharmaceutical formulation is the ratio of the target cell killing activity of the pharmaceutical preparation sample to be subjected to stability test (testing sample) to that of the reference sample.

In some embodiments, the functional activity of a pharmaceutical formulation can be measured by a cytotoxicity test comprising the steps of:
1. 3000 A549 cells (50 μl) were added to a 96-well plate, and 40-fold lymphocytes (50 μl) were then added;
2. the initial concentrations of the testing sample and reference sample of the pharmaceutical formulation were diluted to 10 μg/ml respectively, and then were serially diluted 6 gradients in 10-fold to obtain a total of 7 concentration gradients. Samples at 20 μl/well were added to 96-well plate;
3. after incubating the above 96-well plate in incubator at 37° C. for 4 hours, 50 μl of the supernatant of the cell culture was transferred to another 96-well plate and chromogenic agent was added at 50 μl/well to the 96-well plate and then incubated at room temperature in the dark for 20 minutes;
4. a stop solution was added at 50 μl/well and ED value was recorded by reading at 490 nm within 1 hour. The relative value of the testing sample was calculated from the ED values of the testing sample and the reference sample:

Functional activity (%)=ED value of testing sample/
ED value of reference sample×100%.

In some embodiments, a stable pharmaceutical formulation means that in the test of high temperature stability, light stability, freeze-thaw stability, long-term stability or dilution stability, the binding activity of antibody is 65%-150%. The binding activity indicates the specific binding activity of the antibody to the target, which can be measured by enzyme-linked immunosorbent assay according to General Principle 3418 of Part III of the Chinese Pharmacopoeia (2010 edition).

In some embodiments, the binding activity of antibody is measured by enzyme-linked immunosorbent assay comprising the steps of:
1. the reference sample and testing sample were diluted with the primary antibody dilution to the following 8 gradients: 0.1 ng/ml, 1 ng/ml, 10 ng/ml, 50 ng/ml, 100 ng/ml, 500 ng/ml, 1000 ng/ml and 10000 ng/ml;
2. the diluted solutions of reference sample and testing sample were added to a coated 96-well plate at 100 μl/well, reacted at 37° C. for 1 hour, washed for 3 times and dried;
3. the Ap-goat anti-human IgG (H+L) antibody was diluted 1000-fold with the secondary antibody dilution and was added to a coated 96-well plate at 100μ/well, reacted at 37° C. for 0.5 hour, washed for 3 times and dried;
4. the reaction substrate pNPP (p-nitrophenol phosphate) was added to a coated 96-well plate at 100μ/well, reacted at room temperature in the dark for 20 minutes and read at 405 nm.
5. a four-parameter curve fitting was performed for the standard and testing sample respectively using the absorbance as Y-axis and the concentration of the reference sample solution as X-axis, to obtain the half effective concentration (EC50) of the standard and testing sample. The relative binding activity of the testing sample was calculated according to the following equation:

Relative binding activity (%)=EC50 of testing
sample/EC50 of standard sampler 100%

Formulation Preparation

In another aspect, the present disclosure provides a method for preparing the pharmaceutical formulation, comprising:
1) solution preparation:
  a) preparing an ultrafiltration buffer at a concentration of 5-25 mmol/L;

b) preparing a first formulation solvent comprising a buffer, a protein protective agent and a surfactant, wherein the concentration of the buffer in the first formulation solvent is 5-50 mmol/L, the concentration of the protein protective agent in the first formulation solvent is 60-1200 mmol/L, and the concentration of the surfactant in the first formulation solvent is 1.2-4.8 mg/ml;

c) preparing a second formulation solvent comprising a buffer, a protein protective agent and a surfactant, wherein the concentration of the buffer in the second formulation solvent is 5-50 mmol/L, the concentration of the protein protective agent in the second formulation solvent is 10-200 mmol/L and the concentration of the surfactant in the second formulation solvent is 0.2-0.8 mg/ml;

2) concentrating bulk of monoclonal anti-CD147 antibody to obtain a first solution of monoclonal anti-CD147 antibody having a concentration of monoclonal anti-CD147 antibody of 30-100 mg/ml;

3) injecting the first solution of monoclonal anti-CD147 antibody into an ultrafiltration system and conducting a continuous solvent exchange by six-fold volume using the ultrafiltration buffer to obtain a second solution of monoclonal anti-CD147 antibody;

4) adding the first formulation solvent into the second solution of monoclonal anti-CD147 antibody to obtain the pharmaceutical formulation having a concentration of monoclonal anti-CD147 antibody of 1-40 mg/ml.

In some embodiments, the method further comprises:

5) adding the second formulation solvent into the pharmaceutical formulation obtained in above step 4) such that the concentration of the monoclonal anti-CD147 antibody reaches 15-25 mg/ml.

Uses

In another aspect, the present disclosure further provides a method of treating a disease in a subject, comprising administering a therapeutically effective amount of the pharmaceutical formulation of the present disclosure to a subject, wherein the subject has a disease requiring treatment with an antibody against CD147.

As used herein, the term "treating" refers to reducing or ameliorating the disease or the severity and/or duration of one or more symptoms, inhibiting or preventing the progression of the disease, causing the disease to subside, and inhibiting or preventing recurrence, development, onset or progression of one or more symptoms associated with the disease. The subject in need of treatment comprises a subject already suffering from a disease.

The term "therapeutically effective amount" refers to the minimum concentration required to effect a measurable amelioration or prevention of a particular disease.

The pharmaceutical formulation of the present disclosure can be used to treat CD147-associated diseases, including chronic and acute diseases. CD147-associated diseases include cancer, inflammation and the like. In some embodiments, the CD147-associated disease is, for example, an epithelial-derived malignancy. In some embodiments, the CD147-associated disease is, for example, lung cancer, liver cancer, cervical cancer, colon cancer, breast cancer, ovarian cancer, esophageal cancer or gastric cancer. In some embodiments, the CD147-associated disease is, for example, rheumatoid arthritis. In some embodiments, the CD147-associated disease is non-small cell lung cancer.

The pharmaceutical formulation of the present disclosure can be administered to a subject via any suitable routes. For example, the pharmaceutical formulation can be administered to a subject by subcutaneous injection.

In yet another aspect, the present disclosure provides use of the pharmaceutical formulation in manufacture of a medicament for the treatment of a CD147-associated disease.

The embodiments of the present disclosure further include but are not limited to the following items:

Item 1. A pharmaceutical formulation comprising a monoclonal anti-CD147 antibody, a buffer, a protein protective agent and a surfactant.

Item 2. The pharmaceutical formulation of item 1, wherein the monoclonal anti-CD147 antibody comprises a heavy chain variable region and/or a light chain variable region, and the heavy chain variable region comprises the CDR sequences shown below:

a CDR1 comprising the amino acid sequence of SEQ ID NO: 1;

a CDR2 comprising the amino acid sequence of SEQ ID NO: 2; and a CDR3 comprising the amino acid sequence of SEQ ID NO: 3;

and the light chain variable region comprises the CDR sequences shown below:

a CDR1 comprising the amino acid sequence of SEQ ID NO: 4;

a CDR2 comprising the amino acid sequence of SEQ ID NO: 5; and a CDR3 comprising the amino acid sequence of SEQ ID NO: 6.

Item 3. The pharmaceutical formulation of any one of the preceding items, wherein the monoclonal anti-CD147 antibody is a human murine chimeric monoclonal anti-CD147 antibody.

Item 4. The pharmaceutical formulation of any one of the preceding items, wherein the heavy chain variable region of the monoclonal anti-CD147 antibody comprises the amino acid sequence of SEQ ID NO: 7, SEQ ID NO: 8, SEQ ID NO: 9 or SEQ ID NO: 10.

Item 5. The pharmaceutical formulation of any one of the preceding items, wherein the light chain variable region of the monoclonal anti-CD147 antibody comprises the amino acid sequence of SEQ ID NO: 11, SEQ ID NO: 12, SEQ ID NO: 13 or SEQ ID NO: 14.

Item 6. The pharmaceutical formulation of any one of the preceding items, wherein the monoclonal anti-CD147 antibody comprises a heavy chain comprising the amino acid sequence of SEQ ID NO: 15, SEQ ID NO: 16, SEQ ID NO: 17, or SEQ ID NO: 18 and/or a light chain comprising the amino acid sequence of SEQ ID NO: 19, SEQ ID NO: 20, SEQ ID NO: 21, or SEQ ID NO: 22.

Item 7. The pharmaceutical formulation of any one of the preceding items, wherein the pharmaceutical formulation has a pH of 5.0-8.0, 5.0-6.0, 6.0-7.0 or 7.0-8.0.

Item 8. The pharmaceutical formulation of any one of the preceding items, wherein the concentration of the monoclonal anti-CD147 antibody in the pharmaceutical formulation is 1-40 mg/ml, 1-15 mg/ml, 15-25 mg/ml or 25-40 mg/ml.

Item 9. The pharmaceutical formulation of any one of the preceding items, wherein the buffer is selected from one or more of succinate buffer, histidine buffer, citrate buffer and acetate buffer.

Item 10. The pharmaceutical formulation of any one of the preceding items, wherein the concentration of the buffer is 5-50 mmol/L, 5-11 mmol/L, 11-25 mmol/L or 25-50 mmol/L.

Item 11. The pharmaceutical formulation of any one of the preceding items, wherein the pharmaceutical formulation has a pH of 5.0-6.0, and the buffer is a succinate buffer at a concentration of 11-25 mmol/L.

Item 12. The pharmaceutical formulation of any one of the preceding items, wherein the protein protective agent is selected from one or more of sucrose and trehalose.

Item 13. The pharmaceutical formulation of any one of the preceding items, wherein the pharmaceutical formulation does not comprise an alcoholic protein protective agent.

Item 14. The pharmaceutical formulation of any one of the preceding items, wherein the concentration of the protein protective agent in the pharmaceutical formulation is 10-200 mg/ml, 10-70 mg/ml, 70-80 mg/ml, or 80-200 mg/ml.

Item 15. The pharmaceutical formulation of any one of the preceding items, wherein the protein protective agent is trehalose and the concentration of trehalose in the pharmaceutical formulation is 70-80 mg/ml.

Item 16. The pharmaceutical formulation of any one of the preceding items, wherein the surfactant is selected from one or more of polysorbate 20 and polysorbate 80.

Item 17. The pharmaceutical formulation of any one of the preceding items, wherein the concentration of the surfactant in the pharmaceutical formulation is 0.2-0.8 mg/ml, 0.2-0.35 mg/ml, 0.35-0.45 mg/ml or 0.45-0.8 mg/ml.

Item 18. The pharmaceutical formulation of any one of the preceding items, wherein the surfactant is polysorbate 20 and the concentration of polysorbate 20 in the pharmaceutical formulation is 0.35-0.45 mg/ml.

Item 19. The pharmaceutical formulation of any one of the preceding items, wherein the concentration of the monoclonal anti-CD147 antibody in the pharmaceutical formulation is 15-25 mg/ml;
the buffer is a succinate buffer and the concentration of the succinate buffer is 11-25 mmol/L;
the protein protective agent is trehalose and the concentration of the trehalose in the pharmaceutical formulation is 70-80 mg/ml;
the surfactant is polysorbate 20 and the concentration of polysorbate 20 in the pharmaceutical formulation is 0.35-0.45 mg/ml; and
wherein the pharmaceutical formulation has a pH of 5.0-6.0.

Item 20. The pharmaceutical formulation of any one of the preceding items, wherein the pharmaceutical formulation is stable at low temperature condition for at least 6 months.

Item 21. The pharmaceutical formulation of item 20, wherein the temperature of the low temperature condition is 2-8° C.

Item 22. The pharmaceutical formulation of any one of the preceding items, wherein the pharmaceutical formulation can be diluted 30-50 times by a diluent and remains stable at a temperature of 25±2° C. for at least 8 hours.

Item 23. The pharmaceutical formulation of item 22, wherein the diluent is 0.9% NaCl injection.

Item 24. The pharmaceutical formulation of any one of the preceding items, wherein the pharmaceutical formulation remains stable for up to 10 days at an illumination of not less than 4500 lux at a temperature of 2-8° C.

Item 25. The pharmaceutical formulation of any one of the preceding items, wherein the pharmaceutical formulation is an injection.

Item 26. A use of the pharmaceutical formulation of any one of items 1-25 in the manufacture of a medicament for the treatment of a CD147-associated disease.

Item 27. The use of item 26 wherein the CD147-associated disease is non-small cell lung cancer.

Item 28. A method of preparing the pharmaceutical formulation of any one of item 1-25, comprising:
1) solution preparation:
   a) preparing an ultrafiltration buffer at a concentration of 5-25 mmol/L;
   b) preparing a first formulation solvent comprising a buffer, a protein protective agent and a surfactant, wherein the concentration of the buffer in the first formulation solvent is 5-50 mmol/L, the concentration of the protein protective agent in the first formulation solvent is 60-1200 mmol/L, and the concentration of the surfactant in the first formulation solvent is 1.2-4.8 mg/ml;
   c) preparing a second formulation solvent comprising a buffer, a protein protective agent and a surfactant, wherein the concentration of the buffer in the second formulation solvent is 5-50 mmol/L, the concentration of the protein protective agent in the second formulation solvent is 10-200 mmol/L and the concentration of the surfactant in the second formulation solvent is 0.2-0.8 mg/ml;
2) concentrating bulk of a monoclonal anti-CD147 antibody to obtain a first solution of monoclonal anti-CD147 antibody having a concentration of monoclonal anti-CD147 antibody of 30-100 mg/ml;
3) injecting the first solution of monoclonal anti-CD147 antibody into an ultrafiltration system and conducting a continuous solvent exchange by six-fold volume using the ultrafiltration buffer to obtain a second solution of monoclonal anti-CD147 antibody;
4) adding the first formulation solvent into the second solution of monoclonal anti-CD147 antibody to obtain the pharmaceutical formulation having a concentration of monoclonal anti-CD147 antibody of 1-40 mg/ml.

Item 29. The method of item 28, further comprising:
5) adding the second formulation solvent into the pharmaceutical formulation obtained in above step 4) such that the concentration of the monoclonal anti-CD147 antibody reaches 15-25 mg/ml.

EXAMPLES

The present disclosure can be better understood with reference to the following examples. However, the following examples are intended to illustrate the present disclosure and should not be understood as limiting the scope of the present disclosure. Various changes and modifications may be made in light of the teachings herein, and thus such changes and modifications are within the scope of the present disclosure.

Various reagents, equipments, and measurement methods used in the examples are as follows:

Reagents

Monoclonal anti-CD147 antibody: monoclonal HcHAb18 antibody, comprising a heavy chain of SEQ ID NO: 15 and a light chain of SEQ ID NO: 19.

Succinate buffer: prepared from succinic acid solution and disodium succinate solution.

Histidine buffer: prepared from histidine solution and histidine hydrochloride solution.

Citrate buffer: prepared from citric acid solution and trisodium citrate solution.

Acetate buffer: prepared from acetic acid solution and sodium acetate solution.

Test

In studying the high temperature stability, light stability, freeze-thaw stability and long-term stability of the formulation, the preset standard used in the present disclosure indicating that the formulation is stable is: the change of protein concentration is not more than 2.0 mg/ml (for the initial protein concentration of 20 mg/ml). The protein purity measured by the CE-SDS method is ≥95.5%, the monomer content for the protein purity measured by the SE-HPLC method is 99.00%, the polymer content is the pH of formulation is ≤5.8-6.2, the osmotic pressure of formulation is 300-350 mOsmol/kg, the functional activity of the antibody is 50%-150% and the binding activity of the antibody is 65%-150%.

In studying the accelerated thermal stability of the formulation, the preset standard used in the present disclosure indicating that the formulation is stable is: the protein purity measured by the CE-SDS method is 90.0%.

In studying the oscillation stability of the formulation, the preset standard used in the present disclosure indicating that the formulation is stable is: the increase in polymer content measured by the SE-HPLC method is less than 1.00%.

In studying the dilution stability of the formulation, the preset standard used in the present disclosure indicating that the formulation is stable is: the protein concentration is 0.5±0.05 mg/ml (for the initial protein concentration of the diluted formulation of 0.5 mg/ml). The protein purity measured by the CE-SDS method is ≥95.5%. The monomer content measured by the SE-HPLC method is ≥99.00%. The polymer content is ≤1.00%. The pH of formulation is 5.0-6.0. The functional activity of the antibody is 50%-150%. The binding activity of the antibody is 65%-150%. The amount of insoluble particles having a particle size of 10 µm or more is 6000 particles/ml, and the amount of insoluble particles having a particle size of 25 µm or more is ≤600 particles/ml.

The following table lists the various conditions for testing the stability of the formulation:

| Test | Test conditions | Sampling time |
|---|---|---|
| Accelerated thermal stability | The pharmaceutical formulation is stored at 40 ± 5° C. for 4 weeks. | At Week 0, 1, 2, 3 and 4 |
| Freeze-thaw stability | The pharmaceutical formulation is subjected to three or five cycles, in each cycle the pharmaceutical formulation is kept at −15 ± 5° C. for 2 days and then kept under the accelerated condition at 25 ± 2° C. for 2 days. | At Day 0, 4, 8 and 12, or Day 0, 4 and 20 |
| Oscillation stability | The pharmaceutical formulation is oscillated at a rotation speed of 67 rpm at room temperature for 24 hours. | At Hour 0, 3, 6 and 24 |
| Light Stability | The pharmaceutical formulation is stored at 5 ± 3° C. under an illumination of 4500 ± 500 Lux for 10 days. | At Day 0, 5 and 10 |
| Long-term stability | The pharmaceutical formulation is sealed and stored at 2-8° C. in the dark for 6 months. | At Month 0, 3 and 6 |
| Dilution stability | The pharmaceutical formulation is diluted with 0.9% NaCl injection and then stored at 25 ± 2° C. for 8 hours. | At Hour 0, 0.5, 1, 2, 4 and 8 |
| High temperature stability | The pharmaceutical formulation is stored at 40 ± 2° C. for 10 days. | At Day 0, 5 and 10 |

Measurement of protein concentration: UV-Vis spectrophotometry (detection wavelength: 280 nm)

Measurement of protein purity: CE-SDS, SE-HPLC

Measurement of antibody binding activity: enzyme-linked immunosorbent assay

Measurement of antibody functional activity: Cytotoxicity assay

Example 1: Stability of Monoclonal Anti-CD147 Antibody at Different pH

The monoclonal anti-CD147 antibody at a concentration of 1.5 mg/ml was placed in the histidine-histidine hydrochloride buffer (prepared from 25 mmol/L histidine solution and 25 mmol/L histidine hydrochloride solution) having a pH of 3.5, 4.0, 4.5, 5.0, 5.5, 6.0, 6.5, 7.0, 7.5, 8.0, 8.5 or 9.0, and the Tm of the antibody was measured with differential scanning calorimeter (DSC). The test results are shown in Table 1 and FIG. 1.

TABLE 1

DSC scanning data of monoclonal anti-CD147 antibody at different pHs

| pH | Tm1 (° C.) | Tm2 (° C.) | Tm3 (° C.) |
|---|---|---|---|
| 3.5 | 35.4 | 62.4 | /* |
| 4.0 | 47.2 | 67.5 | /* |
| 4.5 | 52.6 | 72.8 | /* |
| 5.0 | 64.7 | 75.1 | 81.4 |
| 5.5 | 65.1 | 75.2 | 82.7 |
| 6.0 | 66.2 | 75.6 | 82.4 |
| 6.5 | 64.2 | 71.3 | 82.1 |
| 7.0 | 58.1 | 70.4 | 81.3 |
| 7.5 | 55.3 | 69.7 | 81.3 |
| 8.0 | 52.7 | 68.3 | 81.1 |
| 8.5 | /* | 72.1 | /* |
| 9.0 | /* | 74.5 | /* |

*Not detected

Theoretically, three Tm values should be obtained by DSC scanning the monoclonal anti-CD147 antibody, and correspond to three different domains of the antibody, respectively. However, in the DSC scan of this example, the samples at some pH values did not show three Tm values, indicating that some domains of the antibody have been denatured or destroyed under these pH conditions, in other words, these pH conditions are not favorable for the stability of the antibody.

As shown in Table 1 and FIG. 1, the monoclonal anti-CD147 antibody shows three Tm values at a pH of 5.0-8.0, whereas the monoclonal anti-CD147 antibody does not show three Tm values at a pH lower than 5.0 or higher than 8.0. This indicates that the monoclonal anti-CD147 antibody is stable at pH 5.0-8.0. In particular, in the pH range of 5.0-8.0, the values of Tm1, Tm2 and Tm3 of the monoclonal anti-CD147 antibody at pH 5.0-6.0 are significantly higher than those at pH 6.0-8.0, indicating that pH 5.0-6.0 is more beneficial for the stability of monoclonal anti-CD147 antibody. Therefore, for a pharmaceutical formulation comprising a monoclonal anti-CD147 antibody, pH 5.0-6.0 is a preferred pH range for the formulation, and pH 6.0-7.0 and pH 7.0-8.0 are optional pH ranges for the formulation.

Example 2: Effect of Buffer on Formulation Stability

In this example, the following 4 different buffers were selected to prepare pharmaceutical formulations at a pH of 5.0-6.0 comprising a monoclonal anti-CD147 antibody at a concentration of 1.5 mg/ml:

| Buffer | Composition of buffer | pH value |
|---|---|---|
| Succinate buffer | 25 mmol/L succinic acid solution 25 mmol/L disodium succinate solution | 5.0 5.5 6.0 |

-continued

| Buffer | Composition of buffer | pH value |
|---|---|---|
| Histidine buffer | 25 mmol/L histidine solution | 5.0 |
| | 25 mmol/L histidine hydrochloride solution | 5.5 |
| | | 6.0 |
| Citrate buffer | 25 mmol/L citric acid solution | 5.0 |
| | 25 mmol/L trisodium citrate solution | 5.5 |
| | | 6.0 |
| Acetate buffer | 25 mmol/L acetic acid solution | 5.0 |
| | 25 mmol/L sodium acetate solution | 5.5 |
| | | 6.0 |

The Tm of the antibody in the pharmaceutical formulation was measured by DSC, and the pharmaceutical formulation was subjected to the accelerated thermal stability test to analyze the change of protein purity, wherein the protein purity is measured by the CE-SDS method. The results of DSC scan and accelerated thermal stability test are shown in Table 2, Table 3 and FIG. 2. The test results for each group of buffers listed in Tables 2 and 3 are the average of the test results for the formulations comprising the corresponding buffer.

TABLE 2

DSC scan data for formulations comprising a monoclonal anti-CD147 antibody and different buffers.

| Buffer | pH | Tm1 (° C.) | Tm2 (° C.) | Tm3 (° C.) |
|---|---|---|---|---|
| Succinate | 5.0 | 65.1 | 76.2 | 82.8 |
| buffer | 5.5 | 65.5 | 76.9 | 83.1 |
| | 6.0 | 67.3 | 77.1 | 82.9 |
| Histidine buffer | 5.0 | 64.6 | 74.7 | 81.1 |
| | 5.5 | 64.9 | 74.9 | 82.3 |
| | 6.0 | 66.1 | 75.3 | 82.1 |
| Citrate buffer | 5.0 | 64.7 | 74.5 | 81.0 |
| | 5.5 | 64.8 | 74.7 | 82.1 |
| | 6.0 | 65.9 | 75.1 | 82.2 |
| Acetate buffer | 5.0 | 64.3 | 74.3 | 81.4 |
| | 5.4 | 64.6 | 74.5 | 82.2 |
| | 5.8 | 65.9 | 75.1 | 82.1 |

TABLE 3

Results of accelerated thermal stability test for formulations comprising a monoclonal anti-CD147 antibody and different buffers.

| Buffer | Time | Protein purity (%) |
|---|---|---|
| 25 mmol/L pH 5.5 Succinate buffer | Week 0 | 96.3 |
| | Week 1 | 96.2 |
| | Week 2 | 96.1 |
| | Week 3 | 95.9 |
| | Week 4 | 95.5 |
| 25 mmol/L pH 5.5 | Week 0 | 96.1 |
| | Week 1 | 96.1 |
| Histidine buffer | Week 2 | 95.7 |
| | Week 3 | 95.3 |
| | Week 4 | 94.7 |
| 25 mmol/L pH 5.5 Citrate buffer | Week 0 | 96.2 |
| | Week 1 | 95.9 |
| | Week 2 | 95.6 |
| | Week 3 | 95.4 |
| | Week 4 | 94.0 |
| 25 mmol/L pH 5.5 Acetate buffer | Week 0 | 96.3 |
| | Week 1 | 95.6 |
| | Week 2 | 95.0 |
| | Week 3 | 93.7 |
| | Week 4 | 92.1 |

As shown in Table 2, at pH 5.0-6.0, the monoclonal anti-CD147 antibody in succinate buffer showed the highest Tm value, which indicates that compared with the other three buffers, the monoclonal anti-CD147 antibody in succinate buffer had better thermodynamic stability and theoretically had a longer shelf life.

Figure 2:
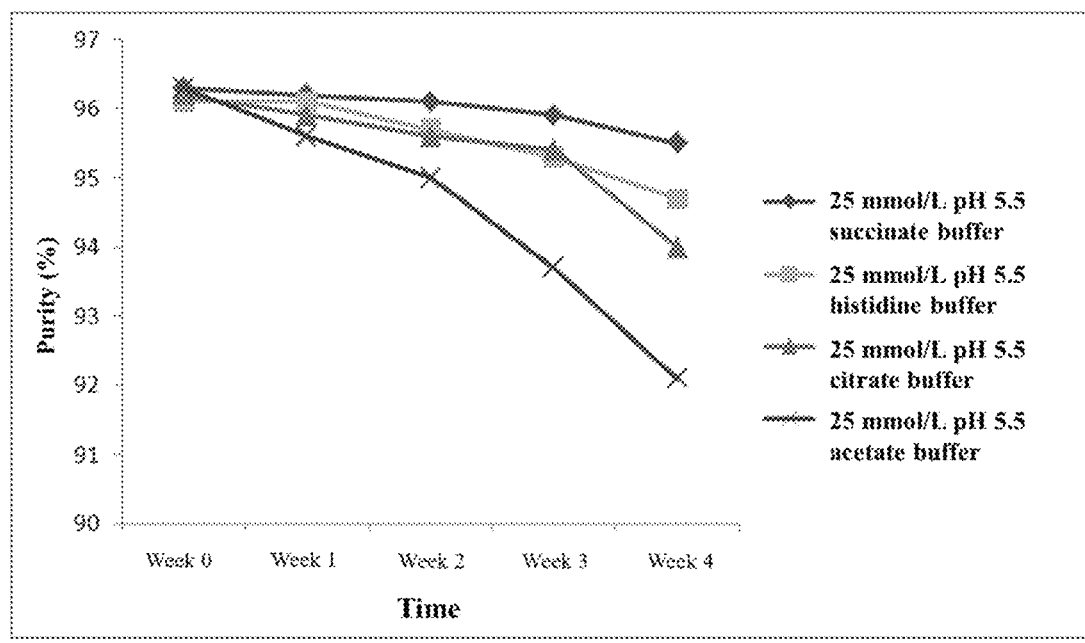
FIG. 2 shows the change of the protein purity measured by the CE-SDS method for the formulation comprising a monoclonal anti-CD147 antibody and different buffers over time in an accelerated thermal stability test.

From the accelerated thermal stability test shown in Table 3 and FIG. 2, it can be seen that the protein purity for formulations comprising four buffers decreased under the test condition within 4 weeks, but the final protein purity are all ≥90.0%. The decrease in protein purity for the formulation comprising succinate buffer is the smallest after 4 weeks, indicating that the succinate buffer provides the best protection for monoclonal anti-CD147 antibody.

Therefore, the succinate buffer can be used as the most preferred buffer for the formulation of the present disclosure comprising a monoclonal anti-CD147 antibody, while histidine buffer, citrate buffer and acetate buffer can be used as optional buffers.

Examples 3: Effect of Buffer Concentration on pH Stability of Formulations

In this example, succinate buffer and histidine buffer at concentrations in three different ranges (5-11 mmol/L, 11-25 mmol/L and 25-50 mg/ml) were selected to prepare formulations at pH 5.5 comprising a monoclonal anti-CD147 antibody at a concentration of 20.0 mg/ml. The formulations were subjected to the accelerated thermal stability test, and pH of the formulations was measured. The obtained results of the accelerated thermal stability test are shown in Table 4. Succinate buffers at different concentrations were prepared from succinic acid solutions and disodium succinate solutions having corresponding concentrations and adjusted to pH 5.5. Histidine buffers at different concentrations were prepared from histidine solutions and histidine hydrochloride solutions having corresponding concentrations and adjusted to pH 5.5. The test results for each group of buffers listed in Table 4 are the average of the test results of the formulations comprising the corresponding buffers.

TABLE 4 pH results of formulations comprising a monoclonal anti-CD147 antibody and buffers at different concentrations in the accelerated thermal stability test

| Buffer | Concentration of buffer (mmol/L) | pH value (Target value: 5.5 ± 0.2, Acceptable range: 5.0-6.0) | | | | | Change of pH |
|---|---|---|---|---|---|---|---|
| | | Week 0 | Week 1 | Week 2 | Week 3 | Week 4 | |
| Succinate buffer | 10 | 5.6 | 5.6 | 5.5 | 5.4 | 5.4 | 0.2 |
| | 25 | 5.6 | 5.6 | 5.6 | 5.6 | 5.6 | 0 |
| | 50 | 5.5 | 5.5 | 5.3 | 5.2 | 5.2 | 0.3 |

TABLE 4-continued pH results of formulations comprising a monoclonal anti-CD147 antibody and buffers at different concentrations in the accelerated thermal stability test

| Buffer | Concentration of buffer (mmol/L) | pH value (Target value: 5.5 ± 0.2, Acceptable range: 5.0-6.0) | | | | | Change of pH |
|---|---|---|---|---|---|---|---|
| | | Week 0 | Week 1 | Week 2 | Week 3 | Week 4 | |
| Histidine buffer | 10 | 5.5 | 5.5 | 5.5 | 5.3 | 5.2 | 0.3 |
| | 25 | 5.5 | 5.5 | 5.5 | 5.4 | 5.4 | 0.1 |
| | 50 | 5.5 | 5.5 | 5.3 | 5.3 | 5.2 | 0.3 |

As shown in Table 4, the pH of the formulation can be stabilized within the range of 5.0-6.0 by using the succinate buffer or histidine buffer at a concentration of 5-50 mmol/L. Compared with the buffer concentrations of 5-11 mmol/L and 25-50 mmol/L, the succinate buffer or histidine buffer at a concentration of 11-25 mmol/L can make the pH of the formulation more stable. The changes in the pH of the formulation within 4 weeks were 0 and 0.1, respectively. Particularly, the succinate buffer at a concentration of 11-25 mmol/L can make the pH of the formulation most stable.

Therefore, 11-25 mmol/L is a more preferred buffer concentration, and 5-11 mmol/L and 25-50 mmol/L are optional buffer concentrations.

As shown in Examples 1-3, the most preferable buffer for the formulation comprising a monoclonal anti-CD147 antibody of the present disclosure is the succinate buffer at a concentration of 11-25 mmol/L, which can make the pH of the pharmaceutical formulation be 5.0-6.0.

Examples 4: Effect of Protein Protective Agent on Formulation Stability

The succinate buffer and histidine buffer at a concentration of 25 mmol/L and three different protein protective agents (trehalose, sucrose and sorbitol) in three different concentration ranges (10-70 mg/ml, 70-80 mg/ml and 80-200 mg/ml) of the protein protective agents were used to prepare the formulation at pH 5.5 comprising a monoclonal anti-CD147 antibody at a concentration of 1.5 mg/ml and different buffers. Tm of the antibody was measured by DSC. The experimental groups of formulations comprising a monoclonal anti-CD147 antibody, different buffers and different protein protective agents at different concentrations are shown in Table 5. The DSC scan results are shown in Table 6.

TABLE 5

Experimental groups of formulations comprising a monoclonal anti-CD147 antibody, different buffers and different protein protective agents at different concentrations

| Exp. group no. | Buffer | pH | Protein protective agent | Concentration of protein protective agent (mg/ml) |
|---|---|---|---|---|
| A1 | 25 mmol/L Succinate buffer | 5.5 | None | / |
| A2 | | | Trehalose | 42 |
| A3 | | | | 75 |
| A4 | | | | 160 |
| A5 | | | Sucrose | 42 |
| A6 | | | | 75 |
| A7 | | | | 160 |
| A8 | | | Sorbitol | 42 |
| A9 | | | | 75 |
| A10 | | | | 160 |
| B1 | 25 mmol/L | 5.5 | None | / |

TABLE 5-continued

Experimental groups of formulations comprising a monoclonal anti-CD147 antibody, different buffers and different protein protective agents at different concentrations

| Exp. group no. | Buffer | pH | Protein protective agent | Concentration of protein protective agent (mg/ml) |
|---|---|---|---|---|
| B2 | Histidine buffer | | Trehalose | 42 |
| B3 | | | | 75 |
| B4 | | | | 160 |
| B5 | | | Sucrose | 42 |
| B6 | | | | 75 |
| B7 | | | | 160 |
| B8 | | | Sorbitol | 42 |
| B9 | | | | 75 |
| B10 | | | | 160 |

TABLE 6

DSC scan data for formulations comprising a monoclonal anti-CD147 antibody, different buffers and different protein protective agents at different concentrations

| Group no. | Tm1 (° C.) | Tm2 (° C.) | Tm3 (° C.) |
|---|---|---|---|
| A1 | 65.5 | 76.9 | 83.1 |
| A2 | 67.2 | 77.4 | 83.9 |
| A3 | 68.1 | 78.1 | 84.1 |
| A4 | 68.7 | 78.4 | 84.3 |
| Tm increase * | 3.2 | 1.5 | 1.2 |
| A5 | 67.0 | 76.7 | 83.6 |
| A6 | 67.8 | 77.4 | 83.7 |
| A7 | 68.1 | 78.1 | 83.3 |
| Tm increase * | 2.6 | 1.2 | 0.6 |
| A8 | 65.3 | 75.6 | 83.1 |
| A9 | 65.5 | 76.1 | 83.3 |
| A10 | 65.9 | 77.1 | 83.3 |
| Tm increase * | 0.4 | 0.2 | 0.2 |
| B1 | 64.3 | 74.9 | 82.3 |
| B2 | 66.8 | 75.7 | 83.5 |
| B3 | 67.2 | 76.2 | 83.7 |
| B4 | 67.7 | 76.9 | 83.4 |
| Tm increase * | 3.4 | 2 | 1.4 |
| B5 | 66.7 | 75.3 | 83.7 |
| B6 | 67.1 | 75.9 | 83.7 |
| B7 | 67.5 | 76.4 | 83.6 |
| Tm increase * | 3.2 | 1.5 | 1.4 |
| B8 | 64.5 | 74.6 | 82.7 |
| B9 | 64.9 | 74.8 | 82.1 |
| B10 | 65.1 | 74.9 | 82.3 |
| Tm increase * | 0.8 | 0 | 0.4 |

* Tm increase refers to the difference between the maximum value of Tm corresponding to a domain of monoclonal anti-CD147 antibody for the formulation comprising a buffer and a protein protective agent and the corresponding Tm value for the control without a protein protective agent.

As shown in Table 6, in the pharmaceutical formulations comprising sucrose and trehalose, the Tm values of the monoclonal anti-CD147 antibody showed increases, indicating that both sucrose and trehalose have the effect of improving the thermodynamic stability of the monoclonal anti-CD147 antibody. In contrast, in the pharmaceutical formulations comprising sorbitol, the increase in the Tm value of the monoclonal anti-CD147 antibody is not significant, indicating that the effect of sorbitol in improving the thermodynamic stability of the monoclonal anti-CD147 antibody is limited.

In addition, compared with the use of histidine buffer as the buffer of the pharmaceutical formulation, the use of succinate buffer can allow the monoclonal anti-CD147 antibody in the formulation to show a relatively higher Tm value, which is consistent with the results of Example 2.

For pharmaceutical formulations comprising succinate buffer, compared with the use of sucrose as the protein protective agent, the use of trehalose as the protein protective agent can allow the monoclonal anti-CD147 antibody to show a relatively higher Tm value. This indicates that trehalose is a more preferred protein protective agent.

When sucrose or trehalose is used as a protein protective agent in the formulation, the concentration of 10-200 mg/ml can make the formulation stability satisfy the preset standard. Trehalose or sucrose at a concentration of 70-80 mg/ml can better maintain osmotic pressure isotonic with the human body. Therefore, the preferred concentration of trehalose or sucrose as a protein protective agent in the pharmaceutical formulation of the present disclosure is 70-80 mg/ml, and the optional concentrations are 10-70 mg/ml and 80-200 mg/ml. Preferably, the formulation of the present disclosure comprises trehalose at a concentration of 70-80 mg/ml as a protein protective agent.

Example 5: Effect of Surfactants on Formulation Stability

Using succinate buffer and trehalose, two different surfactants (polysorbate 80, polysorbate 20) at a concentration within three different concentration ranges (0.2-0.35 mg/ml, 0.35-0.45 mg/ml, and 0.45-0.8 mg/ml) of surfactant were selected in this example to prepare the formulations comprising a monoclonal anti-CD147 antibody at a concentration of 20.0 mg/ml, succinate buffer at a concentration of 25 mmol/L and trehalose at a concentration of 75 mg/ml. For the purpose of comparison, a control formulation having the same other components but without surfactant was also prepared. The experimental groups of the formulations comprising a monoclonal anti-CD147 antibody, succinate buffer, trehalose protein protective agent and different surfactants at different concentrations is shown in Table 7. The above formulations were subjected to oscillation stability test and freeze-thaw stability test. The obtained results of oscillation stability test are shown in Table 8 and FIG. 3, and the obtained results of freeze-thaw stability test are shown in Table 9 and FIG. 4.

TABLE 7

Experimental groups of the formulations comprising a monoclonal anti-CD147 antibody, succinate buffer, trehalose protein protective agent and different surfactants at different concentrations

| Exp. group no. | Composition buffer | Protein of protective agent | Surfactant | Concentration of surfactant (mg/ml) |
|---|---|---|---|---|
| 1 | 25 mmol/L pH 5.5 | 75 mg/ml Trehalose | Polysorbate 80 | 0.25 |
| 2 | Succinate buffer | | Polysorbate 20 | 0.25 |
| 3 | | | Polysorbate 80 | 0.4 |
| 4 | | | Polysorbate 20 | 0.4 |
| 5 | | | Polysorbate 80 | 0.8 |
| 6 | | | Polysorbate 20 | 0.8 |
| Control | 25 mmol/L pH 5.5 Succinate buffer | 75 mg/ml Trehalose | / | / |

TABLE 8

Results of polymer content (%) measured by the SE-HPLC method for the formulations comprising a monoclonal anti-CD147 antibody, succinate buffer, trehalose protein protective agent and different surfactants at different concentrations in the oscillation stability test

| Time | Exp. group 1 | Exp. group 2 | Exp. group 3 | Exp. group 4 | Exp. group 5 | Exp. group 6 | Control group |
|---|---|---|---|---|---|---|---|
| 0 h | 0.41 | 0.41 | 0.41 | 0.41 | 0.41 | 0.41 | 0.41 |
| 3 h | 0.41 | 0.41 | 0.41 | 0.42 | 0.42 | 0.42 | 0.43 |
| 6 h | 0.51 | 0.52 | 0.44 | 0.45 | 0.44 | 0.46 | 0.55 |
| 24 h | 0.56 | 0.54 | 0.51 | 0.47 | 0.48 | 0.49 | 0.62 |
| Content increase | 0.15 | 0.13 | 0.10 | 0.06 | 0.07 | 0.08 | 0.21 |

TABLE 9

Results of polymer content (%) measured by the SE-HPLC method for the formulations comprising a monoclonal anti-CD147 antibody, succinate buffer, trehalose protein protective agent and different surfactants at different concentrations in the freeze-thaw stability test

| Cycles of freeze-thaw | Exp. group 1 | Exp. group 2 | Exp. group 3 | Exp. group 4 | Exp. group 5 | Exp. group 6 | Control group |
|---|---|---|---|---|---|---|---|
| 0 | 0.41 | 0.41 | 0.41 | 0.41 | 0.41 | 0.41 | 0.41 |
| 1 | 0.49 | 0.48 | 0.46 | 0.47 | 0.51 | 0.49 | 0.52 |
| 5 | 0.87 | 0.97 | 0.84 | 0.82 | 0.85 | 0.81 | 1.22 |
| Content increase | 0.46 | 0.56 | 0.43 | 0.41 | 0.44 | 0.40 | 0.81 |

Figure 3:
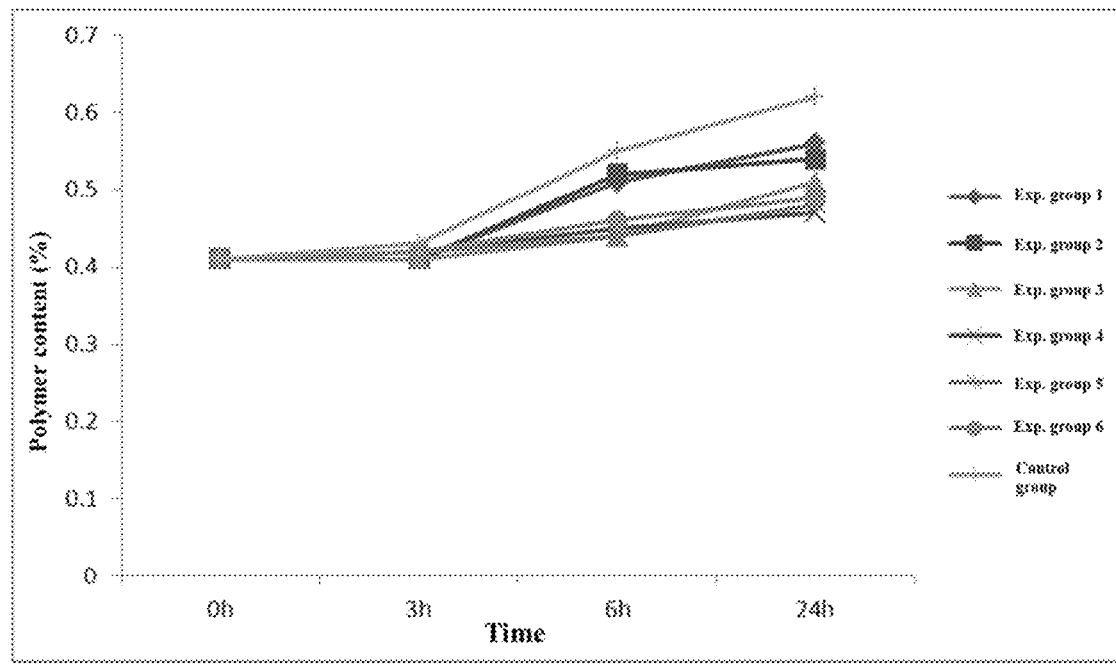
FIG. 3 shows the change of the polymer content measured by the SE-HPLC method for the formulation comprising a monoclonal anti-CD147 antibody, a succinate buffer, trehalose protein protective agent and different surfactants over time in an oscillation stability test.

As shown in Table 8 and FIG. 3, the increase in polymer content for experimental groups 1-6 was significantly less than that for the control group without surfactant, indicating that both the polysorbate 80 and polysorbate 20 at a concentration of 0.2-0.8 mg/ml have the effect of slowing down the increase of the polymers of antibody. The increase in polymer content for experimental group 4 comprising polysorbate 20 is the smallest, that is, 0.06%.

Figure 4:
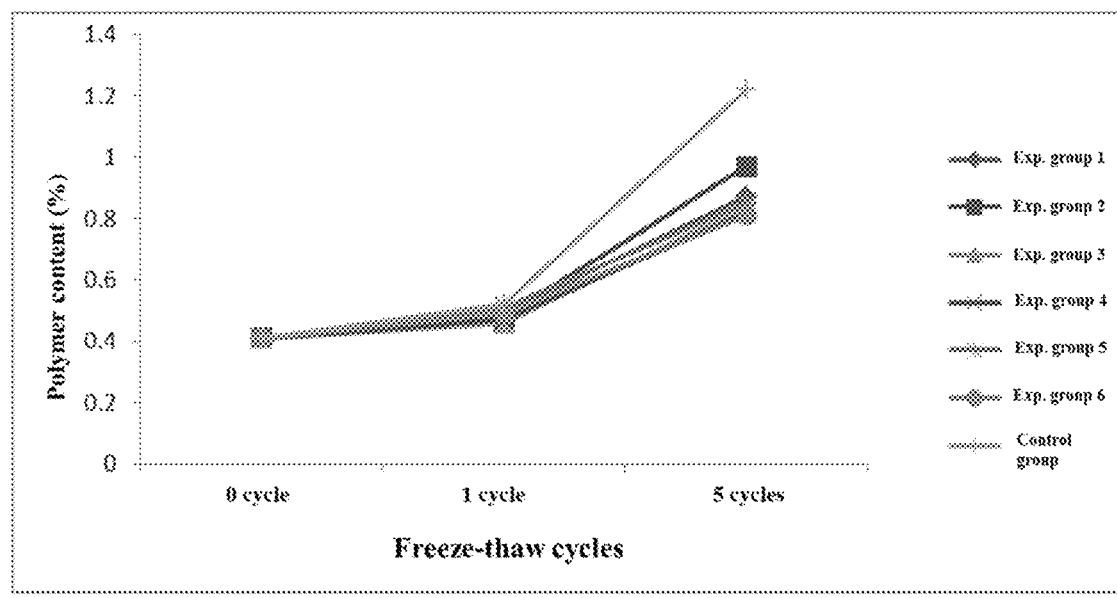
FIG. 4 shows the change of the polymer content measured by the SE-HPLC method for the formulation comprising a monoclonal anti-CD147 antibody, a succinate buffer, trehalose protein protective agent and different surfactants over time in a freeze-thaw stability test.

As shown in Table 9 and FIG. 4, the increase in polymer content for experimental groups 1-6 after freeze-thaw was significantly less than that for the control group without surfactant, indicating that both the polysorbate 80 and polysorbate 20 at a concentration of 0.2-0.8 mg/ml have the effect of slowing down the increase of polymers of antibody. The increase in polymer content for experimental group 6 comprising polysorbate 20 is the smallest, that is, 0.40%.

From the results of oscillation stability test and freeze-thaw stability test, it can be seen that both polysorbate 80 and polysorbate 20 at a concentration of 0.2-0.8 mg/ml have the effect of slowing down the increase of polymers of antibody. Compared with polysorbate 80, polysorbate 20 is more advantageous to slow down the increase in polymer content. Therefore, polysorbate 20 is the preferred surfactant for the pharmaceutical formulation of the present disclosure. Polysorbate 80 also has the effect of slowing down the increase in polymer content, and thus can be used as an optional surfactant for the pharmaceutical formulation of the present disclosure.

For experimental group 4, the increase in polymer content in the oscillation stability test is only 0.06%, the best among all the experimental groups, and the increase in polymer content in the freeze-thaw stability test is 0.41%, differing the least from that of the optimal group. Therefore, polysorbate 20 at a concentration of 0.35-0.45 mg/ml is the most preferred for the pharmaceutical formulation of the present disclosure, and polysorbate 80 at a concentration of 0.35-0.45 mg/ml can be an optional surfactant for the pharmaceutical formulation of the present disclosure.

Example 6: Factors Affecting the Stability of the Pharmaceutical Formulations of the Present Disclosure The pharmaceutical formulation of the present disclosure was prepared, wherein the concentration of the monoclonal anti-CD147 antibody is 20.0 mg/ml, the concentration of succinate buffer is 25 mmol/L, the concentration of trehalose is 75 mg/ml, the concentration of polysorbate 20 is 0.40 mg/ml and the pH of the formulation is 5.5. The obtained formulation was subjected to influencing factor tests, including high temperature stability test, light stability test and freeze-thaw stability test. The results of each test are shown in Table 10.

TABLE 10

Results of influencing factor tests for the formulations of the present disclosure.

| Test | Time | Protein concentration (mg/ml) | pH of formulation | Osmotic pressure of formulation (mOsmol/kg) | Protein purity (%) CE-SDS method | Protein purity (%) SE-HPLC method Monomer | Protein purity (%) SE-HPLC method Polymer | Functional activity (%) | Binding activity (%) |
|---|---|---|---|---|---|---|---|---|---|
| Preset standard | | 15-25 | 5.0-6.0 | 300-350 | ≥95.5% | ≥99.0% | ≤1.0% | 50-150 | 65-150 |
| High temperature stability test | Day 0 | 20.0 | 6.0 | 313 | 98.1 | 99.79 | 0.21 | 85 | 96 |
| | Day 5 | 19.9 | 6.0 | 314 | 97.8 | 99.71 | 0.29 | 106 | 119 |
| | Day 10 | 19.8 | 5.9 | 312 | 97.4 | 99.69 | 0.31 | 92 | 110 |
| Light stability test | Day 0 | 20.0 | 6.0 | 313 | 98.1 | 99.79 | 0.21 | 85 | 96 |
| | Day 5 | 20.2 | 5.9 | 301 | 97.3 | 98.44 | 1.53 | 85 | 69 |
| | Day 10 | 19.9 | 5.9 | 311 | 96.6 | 97.59 | 2.45 | 77 | 69 |
| Freeze-thaw stability test | Day 0 | 20.0 | 6.0 | 313 | 98.1 | 99.79 | 0.21 | 85 | 96 |
| | Day 4 | 19.9 | 6.0 | 313 | 98.0 | 99.77 | 0.23 | 102 | 97 |
| | Day 8 | 19.8 | 5.9 | 310 | 98.07 | 99.74 | 0.26 | 82 | 96 |

As shown in Table 10, under the test conditions of high temperature stability, light stability and freeze-thaw stability, the protein concentration, pH, osmotic pressure, functional activity and binding activity for the formulations of the present disclosure are all maintained within the range of the preset standards. Under the test condition of high temperature stability, the protein purity (CE-SDS) for the formulation of the present disclosure decreased by 0.7% and the polymer content increased by 0.1%. Under the test condition of light stability, the polymer content for the formulation of the present disclosure increased by 2.24%, and the protein purity (CE-SDS) decreased by 1.5%, indicating that the formulation of the present disclosure should be stored in the dark. Under the test condition of freeze-thaw stability, the protein purity (CE-SDS) for the formulation of the present disclosure decreased by 0.1% and the polymer content increased by 0.05%. At the end of each test, both the purity (CE-SDS) and polymer content for the formulation of the present disclosure comply with the preset standard.

Therefore, the formulation of the present disclosure can maintain the stability of the monoclonal anti-CD147 antibody. In order to better maintain the stability of the antibody, the pharmaceutical formulation of the present disclosure is preferably stored in the dark at a temperature of 2-8° C.

Example 7: Long-Term Stability of the Formulation of the Present Disclosure

Three batches of formulations of the present disclosure were prepared using a monoclonal anti-CD147 antibody, succinate buffer, trehalose and polysorbate 20 and were named as group A, group B and group C, wherein the concentration of the monoclonal anti-CD147 antibody was 20.0 mg/ml, the concentration of succinate buffer was 25 mmol/L, the concentration of trehalose was 75 mg/ml, the concentration of polysorbate 20 was 0.40 mg/ml and the pH of the formulation was 5.5.

Long-term stability tests were performed on the formulations of groups A-C and the results are shown in Table 11. The formulation was placed in an injection vial with the vial top sealed with a bromobutyl rubber plug and fastened with an aluminum-plastic composite cap. The formulation was stored at 2-8° C. in the dark for at least 6 months and samples were periodically taken to measure the protein concentration, purity and others of the formulation.

TABLE 11

Results of long-term stability test for the formulations of the present disclosure

| Group no. | Time | Protein concentration (mg/ml) | Protein purity CE-SDS method (%) | Protein purity SE-HPLC method (%) | | pH of formulation | Osmotic pressure of formulation (mOsmol/kg) | Functional activity (%) | Binding activity (%) |
|---|---|---|---|---|---|---|---|---|---|
| | | | | Monomer | Polymer | | | | |
| | Preset standard | 15-25 | ≥95.5% | ≥99.0% | ≤1.0% | 5.0-6.0 | 300-350 | 50-150 | 65-150 |
| A | Month 0 | 20.0 | 98.1 | 99.79 | 0.21 | 6.0 | 313 | 85 | 96 |
| | Month 3 | 20.1 | 98.0 | 99.68 | 0.32 | 6.0 | 308 | 84 | 115 |
| | Month 6 | 19.5 | 97.9 | 99.67 | 0.33 | 5.9 | 310 | 114 | 88 |
| B | Month 0 | 20.4 | 98.6 | 99.80 | 0.20 | 5.9 | 310 | 102 | 102 |
| | Month 3 | 20.0 | 98.1 | 99.68 | 0.32 | 6.0 | 308 | 95 | 98 |
| | Month 6 | 20.5 | 97.7 | 99.66 | 0.34 | 6.0 | 301 | 109 | 101 |
| C | Month 0 | 20.7 | 98.6 | 99.87 | 0.13 | 6.0 | 324 | 110 | 96 |
| | Month 3 | 20.4 | 98.3 | 99.70 | 0.30 | 6.0 | 320 | 106 | 132 |
| | Month 6 | 20.6 | 98.3 | 99.67 | 0.33 | 6.0 | 316 | 103 | 117 |

As shown in Table 11, there is no significant change in protein concentration, pH, osmotic pressure and functional activity for formulations of groups A-C at the end of 6-month test. The protein purity measured by the CE-SDS method decreased by 0.2%, 0.9% and 0.3%, respectively. The polymer content measured by the SE-HPLC method increased by 0.12%, 0.14% and 0.20%, respectively. The polymer content for formulations of groups A-C satisfied the preset standard and the change of binding activity also satisfied the preset standard. This indicates that the formulation of the present disclosure can be stably stored at 2-8° C. for 6 months.

Example 8: The Dilution Stability of the Formulation of the Present Disclosure

The formulation of the present disclosure was prepared, wherein the concentration of a monoclonal anti-CD147 antibody was 20.0 mg/ml, the concentration of succinate buffer was 25 mmol/L, the concentration of trehalose was 75 mg/ml, the concentration of polysorbate 20 was 0.40 mg/ml and the pH of the formulation was 5.5. The formulation was diluted with 0.9% NaCl injection such that the antibody concentration in the formulation decreased from 20.0 mg/ml to 0.5 mg/ml. The stability of the diluted formulations was tested under the condition of dilute stability test. The dilution stability test was repeated for three times and recorded as group A, B and C. The results are shown in Table 12.

TABLE 12

Results of dilution stability test for the formulations of the present disclosure

| Group no. | Time | Protein purity (%) SE-HPLC method | | Protein purity (%) CE-SDS method | Protein concentration | pH of | Insoluble particles (particles/ml) | | Functional activity | Binding activity |
|---|---|---|---|---|---|---|---|---|---|---|
| | | Monomer | Polymer | (Non-reduction) | (mg/ml) | formulation | 10 μm or more | 25 μm or more | (%) | (%) |
| | Preset standard | ≥99.00% | ≤1.00% | ≥95.5% | 0.5 ± 0.05 | 5.0-6.0 | ≤6000 | ≤600 | 50-150 | 65-150 |
| A | Hour 0 | 99.72 | 0.28 | 98.2 | 0.5 | 5.8 | 154 | 2 | 78 | 107 |
| | Hour 0.5 | / | / | / | 0.5 | 5.8 | 116 | 0 | / | / |
| | Hour 1 | / | / | / | 0.5 | 5.8 | 489 | 3 | / | / |
| | Hour 2 | / | / | / | 0.5 | 5.8 | 217 | 0 | / | / |
| | Hour 4 | 99.72 | 0.28 | 98.2 | 0.5 | 5.8 | 99 | 2 | / | / |
| | Hour 8 | 99.72 | 0.28 | 98.2 | 0.5 | 5.8 | 194 | 2 | 85 | 113 |
| B | Hour 0 | 99.72 | 0.28 | 98.3 | 0.5 | 5.8 | 61 | 0 | 71 | 116 |
| | Hour 0.5 | / | / | / | 0.5 | 5.8 | 106 | 0 | / | / |
| | Hour 1 | / | / | / | 0.5 | 5.8 | 165 | 0 | / | / |
| | Hour 2 | / | / | / | 0.5 | 5.5 | 120 | 0 | / | / |
| | Hour 4 | 99.72 | 0.28 | 98.3 | 0.5 | 5.8 | 134 | 0 | / | / |
| | Hour 8 | 99.72 | 0.28 | 98.6 | 0.5 | 5.8 | 132 | 0 | 78 | 109 |
| C | Hour 0 | 99.76 | 0.24 | 98.3 | 0.5 | 5.8 | 154 | 0 | 66 | 116 |
| | Hour 0.5 | / | / | / | 0.5 | 5.8 | 139 | 1 | / | / |
| | Hour 1 | / | / | / | 0.5 | 5.7 | 194 | 2 | / | / |
| | Hour 2 | / | / | / | 0.5 | 5.6 | 247 | 2 | / | / |
| | Hour 4 | 99.76 | 0.24 | 98.5 | 0.5 | 5.8 | 225 | 2 | / | / |
| | Hour 8 | 99.76 | 0.24 | 98.3 | 0.5 | 5.8 | 101 | 0 | 68 | 95 |

As shown in Table 12, after the dilution of the formulations of groups A-C, the changes in pH, protein concentration, protein purity (CE-SDS method), monomer and polymer contents (SE-HPLC method), insoluble particles, functional activity, and binding activity of formulations all satisfied the preset standard, which indicates that the formulation of the present disclosure after being diluted 40 times with 0.9% NaCl injection can be stably stored at 25±2° C. for at least 8 hours.

The present disclosure is not limited to the scope of the specific embodiments described herein. Indeed, according to the above description, various changes and modifications of the present disclosure are apparent to a person skilled in the art. Such changes and modifications also fall within the scope of the appended claims.

What is claimed is:

1. A pharmaceutical formulation, comprising a monoclonal anti-CD147 antibody, a buffer, a protein protective agent and a surfactant, wherein the buffer is succinate buffer, the protein protective agent is trehalose, and the surfactant is polysorbate 20,
   wherein the monoclonal anti-CD147 antibody comprises a heavy chain comprising the amino acid sequence of SEQ ID NO: 15, SEQ ID NO: 16, SEQ ID NO: 17 or SEQ ID NO: 18 and a light chain comprising the amino acid sequence of SEQ ID NO: 19, SEQ ID NO: 20, SEQ ID NO: 21 or SEQ ID NO: 22, wherein the concentration of the monoclonal anti-CD147 antibody in the pharmaceutical formulation is 20.0 mg/ml,
   wherein the concentration of the succinate buffer is 25 mmol/L, the concentration of the trehalose in the pharmaceutical formulation is 75 mg/ml, the concentration of the polysorbate 20 in the pharmaceutical formulation is 0.40 mg/ml,
   wherein the pharmaceutical formulation has a pH of 5.0-6.0.

2. The pharmaceutical formulation of claim 1, wherein the pharmaceutical formulation remains stable at 2-8° C. for at least 6 months.

3. The pharmaceutical formulation of claim 1, wherein the pharmaceutical formulation can be diluted 30-50 times with a diluent and remains stable for at least 8 hours at 25±2° C.